(12) United States Patent
Tsukagoshi

(10) Patent No.: US 11,866,457 B2
(45) Date of Patent: Jan. 9, 2024

(54) CLEARING AGENT

(71) Applicant: SAVID THERAPEUTICS INC., Tokyo (JP)

(72) Inventor: Masanobu Tsukagoshi, Tokyo (JP)

(73) Assignee: SAVID THERAPEUTICS INC., Tokyo (JP)

( * ) Notice: Subject to any disclaimer, the term of this patent is extended or adjusted under 35 U.S.C. 154(b) by 741 days.

(21) Appl. No.: 16/463,577

(22) PCT Filed: Nov. 24, 2017

(86) PCT No.: PCT/JP2017/042190
§ 371 (c)(1),
(2) Date: Aug. 23, 2019

(87) PCT Pub. No.: WO2018/097239
PCT Pub. Date: May 31, 2018

(65) Prior Publication Data
US 2019/0382435 A1 Dec. 19, 2019

(30) Foreign Application Priority Data
Nov. 25, 2016 (JP) .................... 2016-228810

(51) Int. Cl.
| | |
|---|---|
| C07H 15/26 | (2006.01) |
| A61K 51/04 | (2006.01) |
| A61K 51/08 | (2006.01) |
| A61P 39/00 | (2006.01) |

(52) U.S. Cl.
CPC ......... *C07H 15/26* (2013.01); *A61K 51/0491* (2013.01); *A61K 51/08* (2013.01); *A61P 39/00* (2018.01)

(58) Field of Classification Search
CPC ........ A61K 51/00; A61K 51/04; A61K 51/08; A61K 51/0491; C07H 15/26; A61P 39/00; C07K 14/36; C07D 519/00
USPC ... 424/1.11, 1.65, 1.73, 1.69, 1.81, 85, 1.89, 424/9.1, 9.2, 1.49
See application file for complete search history.

(56) References Cited

U.S. PATENT DOCUMENTS

2003/0129191 A1   7/2003   Theodore et al.

FOREIGN PATENT DOCUMENTS

| EP | 3109252 A1 | 12/2016 |
|---|---|---|
| JP | 2012-167987 | 9/2012 |
| WO | 97/46098 A1 | 12/1997 |
| WO | 2010/095455 | 8/2010 |
| WO | 2015/125820 | 8/2015 |

OTHER PUBLICATIONS

Wilbur et al, Bioconjugate Chemistry, vol. 21, No. 7, pp. 1225-1238 (Year: 2010).*
Extended European Search Report issued in the corresponding European patent application No. 17873351.5, dated Jul. 7, 2020.
Office Action issued in corresponding European patent application No. 17873351.5, dated Feb. 26, 2021.
Hnatowich et al., "J. Nucl. Med., 28", 1987, pp. 1294-1302.
D. S. Wilbur et al., "Design and synthesis of bis-biotin-containing reagents for applications utilizing monoclonal antibody-based pretargeting systems with streptavidin mutants", Bioconjugate Chemistry, vol. 21, No. 7, 2010, pp. 1225-1238.
International Search Report issued in International Pat. Appl. No. PCT/JP2017/042190, dated Jan. 9, 2018.
International Preliminary Report on Patentability issued with respect to International Pat. Appl. No. PCT/JP2017/042190, dated May 28, 2019 (in Japanese and English).
Office Action issued in corresponding Japanese Patent App. No. 2018-552971, dated Nov. 16, 2021, along with an English Machine Translation.
Office Action issued in the corresponding Chinese patent application No. 201780072974.2 dated Dec. 30, 2021, along with English Translation.

(Continued)

*Primary Examiner* — D. L. Jones
(74) *Attorney, Agent, or Firm* — GREENBLUM & BERNSTEIN, P.L.C.

(57) ABSTRACT

It is an object of the present invention to provide a clearing agent, by which after a fusion of the streptavidin mutant and a molecular probe has been administered, the fusion, which is not localized in a target site such as an affected site but remains in the body, can be promptly removed (cleared) from the body. The present invention provides a compound represented by the following formula (1) or a salt thereof:

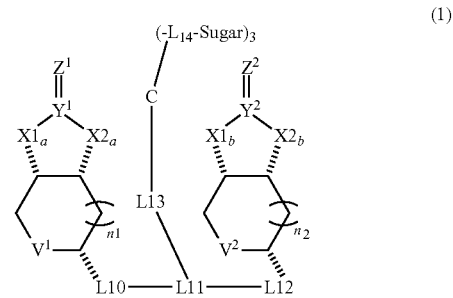

(1)

wherein X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; L10 and L12 each independently represent a divalent linking group; L11 represents a trivalent linking group; L14 represents a divalent linking group; and Sugar represents a sugar residue.

6 Claims, 3 Drawing Sheets
Specification includes a Sequence Listing.

(56) References Cited

OTHER PUBLICATIONS

Wu et al., "Experimental study of SA-gal clearance in tumor radioimmunotherapy," Nuclear Techniques, vol. 24, No. 5, p. 403-407, May 2001.
Yoo et al., "N-Acetylgalactosamino Dendrons as Clearing Agents to Enhance Liver Targeting of Model Antibody-Fusion Protein," Bioconjugate Chem., vol. 24, 2013, p. 2088-2103.
Cheal et al., "Evaluation of Glycodendron and Synthetically Modified Dextran Clearing Agents for Multistep Targeting of Radioisotopes for Molecular Imaging and Radioimmunotherapy," Mol. Pharmaceutics, vol. 11, 2013, p. 400-416.
Office Action issued in the corresponding Chinese patent application No. 201780072974.2 dated Aug. 3, 2022, along with an English language translation.

* cited by examiner

[Fig. 1]
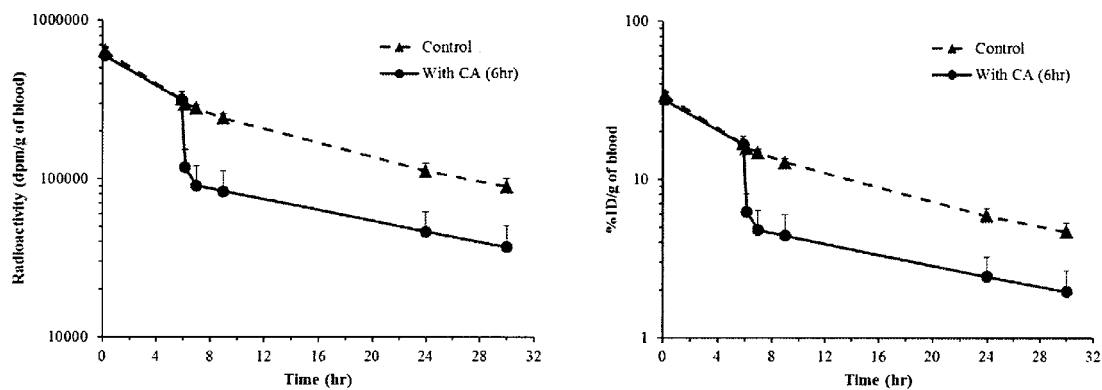
[Fig. 2]
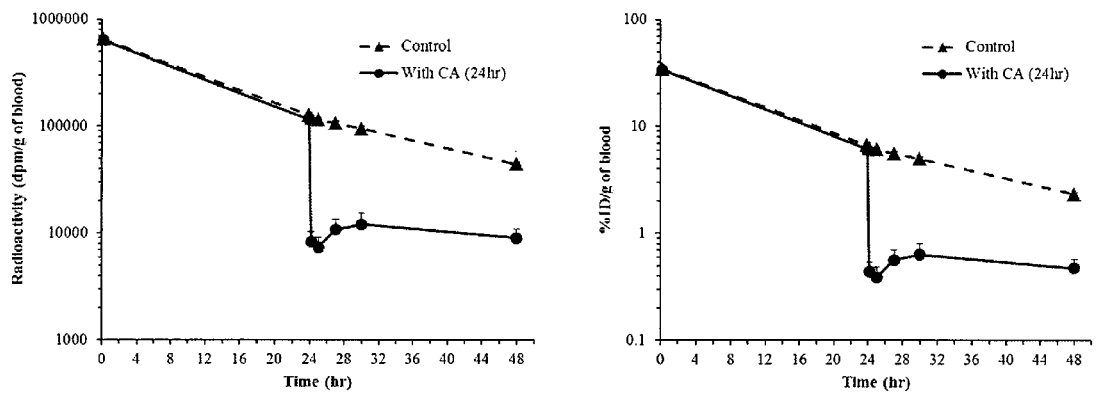

[Fig. 3]
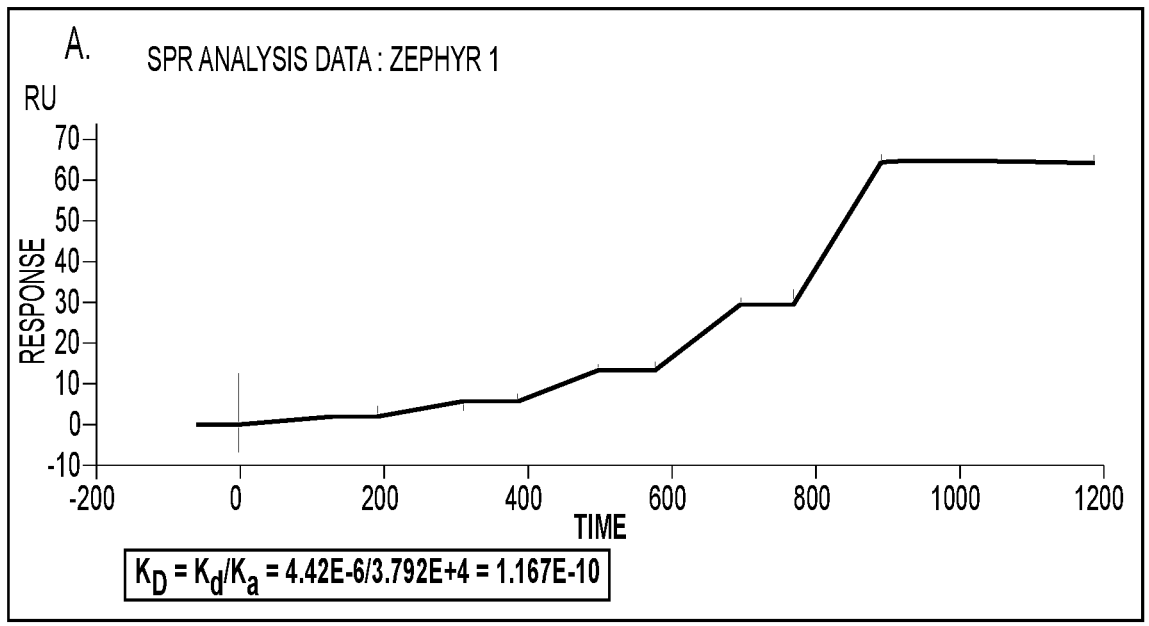
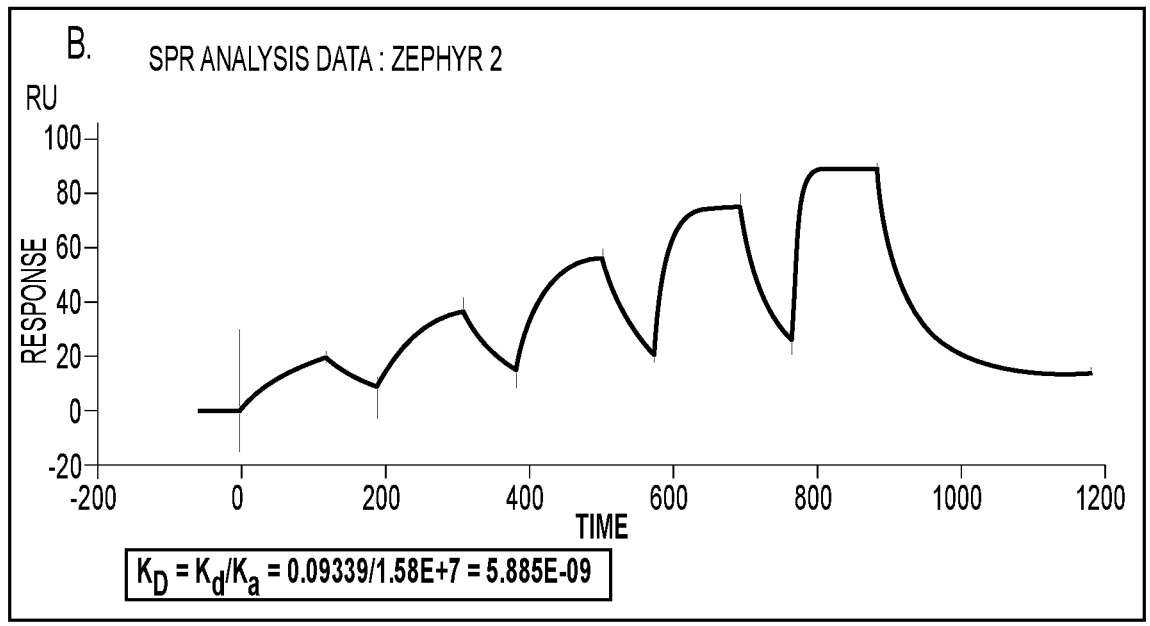

[Fig. 4]
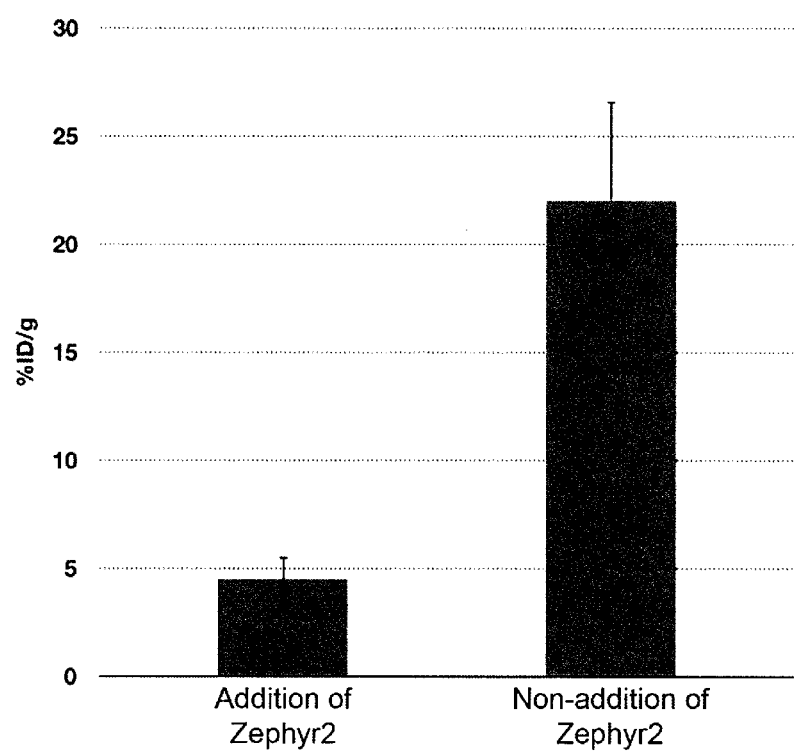

CLEARING AGENT

TECHNICAL FIELD

The present invention relates to a clearing agent for removing a streptavidin mutant from a body, and use thereof.

BACKGROUND ART

The affinity between avidin and biotin, or between streptavidin and biotin, is extremely high, and the interaction of avidin/streptavidin with biotin has been broadly applied in the field of biochemistry, molecular biology or medicine. A drug delivery method and a pretargeting method, in which this high binding ability between avidin/streptavidin and biotin is combined with an antibody molecule, have been devised (Hnatowich, (1987), J. Nucl. Med., 28, 1294-1302).

Chicken-derived avidin or microbe-derived streptavidin exhibits high immunogenicity to human bodies. Thus, low immunogenic streptavidin has been reported (International Publication No. WO 2010/095455). Moreover, a streptavidin mutant having a reduced affinity to natural biotin, and a biotin variant having a high affinity to the aforementioned streptavidin mutant having a low affinity to natural biotin have been reported (International Publication No. WO 2015/125820).

PRIOR ART DOCUMENTS

Patent Documents

Patent Document 1: International Publication No. WO 2010/095455
Patent Document 2: International Publication No. WO 2015/125820

Non-Patent Documents

Non-Patent Document 1: Hnatowich, (1987), J. Nucl. Med., 28, 1294-1302

SUMMARY OF INVENTION

Object to be Solved by the Invention

A pretargeting method, in which the streptavidin mutant having a reduced affinity to natural biotin, which is described in International Publication No. WO 2015/125820, is used in combination with a biotin variant having a high affinity to the aforementioned streptavidin mutant having a reduced affinity to natural biotin, is promising as a novel therapeutic method for diseases such as cancer. In order to realize the above-described pretargeting method, it is desired that, after administration of a fusion of a streptavidin mutant and a molecular probe (an antibody, etc.), the fusion, which is not localized in a target site such as an affected site but remains in the body, is promptly removed (cleared) from the body.

It is an object of the present invention to provide a clearing agent, by which after a fusion of the streptavidin mutant having a reduced affinity to natural biotin described in International Publication No. WO 2015/125820 and a molecular probe has been administered, the fusion, which is not localized in a target site such as an affected site but remains in the body, can be promptly removed (cleared) from the body. In addition, it is another object of the present invention to provide a diagnostic kit and a therapeutic kit, in which the above-described clearing agent is used.

Means for Solving the Object

As a result of intensive studies directed towards achieving the aforementioned objects, the present inventors have found that a fusion of a streptavidin mutant having a reduced affinity to natural biotin and a molecular probe can be promptly removed (cleared) from the body by administration of a compound, in which a plurality of sugar residues bind to the biotin variant dimer described in International Publication No. WO 2015/125820 via linking groups, thereby completing the present invention.

Specifically, according to the present invention, the following inventions are provided.

[1] A compound represented by the following formula (1) or a salt thereof:

[Formula 1]

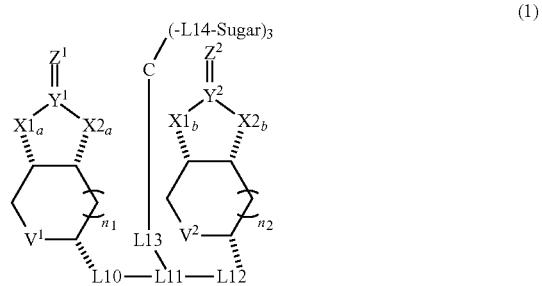

(1)

wherein X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; L10 and L12 each independently represent a divalent linking group; L11 represents a trivalent linking group; L14 represents a divalent linking group; and Sugar represents a sugar residue.

[2] The compound according to the above [1] wherein n1 and n2 each represent 0, which is represented by the following formula (2), or a salt thereof:

[Formula 2]

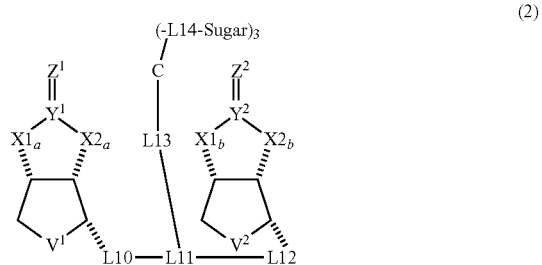

(2)

wherein X1a, X1b, X2a, X2b, $Y^1$, $Y^2$, $Z^1$, $Z^2$, $V^1$, $V^2$, L10, L12, L11, L14, and Sugar have the same meanings as the above [1].

[2] The compound according to the above [1] or [2], which is represented by the following formula (3), or a salt thereof:

[Formula 3]

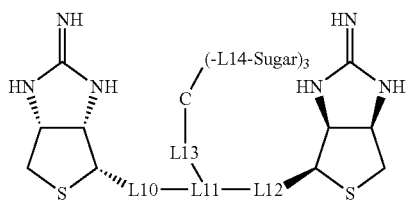
(3)

wherein L10, L12, L11, L14, and Sugar have the same meanings as the above [1].

[4] The compound according to any one of the above [1] to [3], or a salt thereof, wherein L10 and L12 each independently represent an alkylene group containing 1 to 10 carbon atoms, —CONH—, —NHCO—, —O—, or a combination thereof.

[5] The compound according to any one of the above [1] to [4], or a salt thereof, wherein L11 is a group represented by the following formula:

[Formula 4]

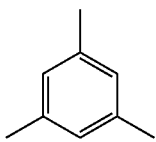

[6] The compound according to any one of the above [1] to [5], or a salt thereof, wherein L13 represents an alkylene group containing 1 to 10 carbon atoms, —CONH—, —NHCO—, —O—, a group represented by the following formula:

[Formula 5]

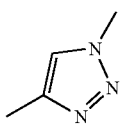

or a combination thereof.

[7] The compound according to any one of the above [1] to [6], or a salt thereof, wherein L14 represents an alkylene group containing 1 to 10 carbon atoms, —CONH—, —NHCO—, —O—, or a combination thereof.

[8] A compound represented by either one of the following formulae, or a salt thereof:

[Formula 6]

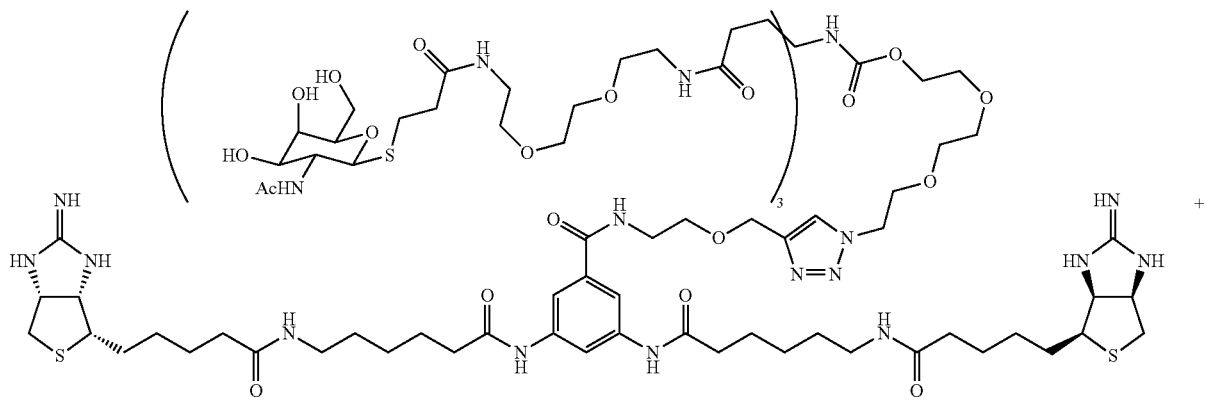

-continued

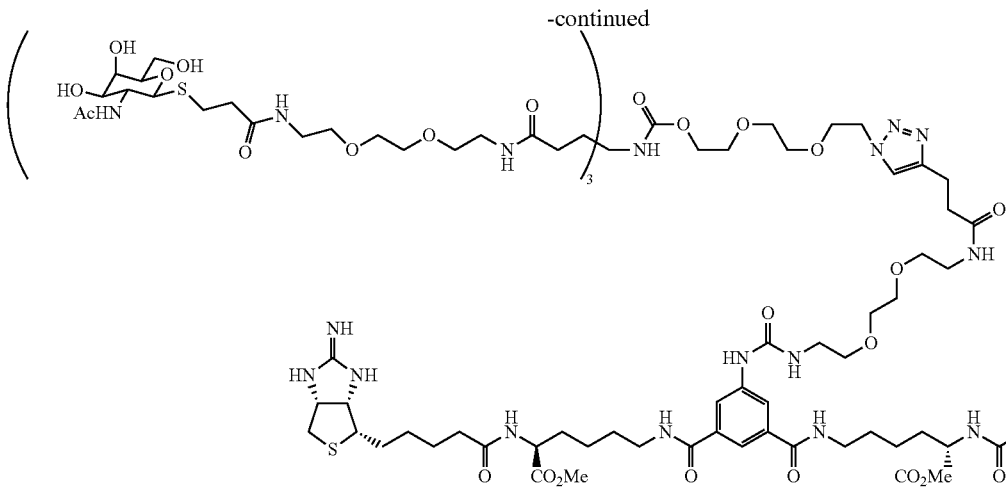

[9] A clearing agent for clearing a fusion of a streptavidin mutant and a molecular probe, comprising the compound according to any one of the above [1] to [8] or a salt thereof.

[10] The clearing agent according to the above [9], wherein the streptavidin mutant consists of the amino acid sequence as set forth in SEQ ID NO: 3, in which the amino acid residue at position 37, Asn, is substituted with another amino acid residue.

[11] The clearing agent according to the above [9] or [10], wherein the streptavidin mutant consists of the amino acid sequence as set forth in SEQ ID NO: 4.

[12] A therapeutic, in vivo diagnostic, or ex vivo diagnostic kit, comprising, at least, the compound according to any one of the above [1] to [8] or a salt thereof, and a fusion of a streptavidin mutant and a molecular probe.

[13] The kit according to the above [12], further comprising a therapeutic, in vivo diagnostic, or ex vivo diagnostic substance, which is labeled with a compound represented by the following formula (10):

[Formula 7]

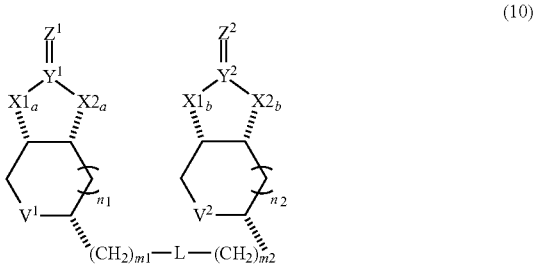

(10)

wherein X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; m1 and m2 each independently represent an integer from 1 to 10; and L represents a linking group.

Advantageous Effects of Invention

According to the present invention, a fusion of a streptavidin mutant having a reduced affinity to natural biotin and a molecular probe can be promptly removed (cleared) from a body.

The clearing agent of the present invention is useful in diagnostic methods and/or therapeutic methods, which are based on a pretargeting method of using a streptavidin mutant in combination with a dimeric compound of biotin variant.

BRIEF DESCRIPTION OF DRAWINGS

FIG. 1 shows the results obtained by analyzing the influence of a clearing agent on mouse blood clearance, in a case where the clearing agent is administered 6 hours after administration of $^{125}$I-labeled pretargeting antibody-Cupid.

FIG. 2 shows the results obtained by analyzing the influence of a clearing agent on mouse blood clearance, in a case where the clearing agent is administered 24 hours after administration of $^{125}$I-labeled pretargeting antibody-Cupid.

FIG. 3 shows the results obtained by measuring the affinity of Compound 14 (Zhepyr1) and Compound 25 (Zephyr2) to Cupid.

FIG. 4 shows the results obtained by confirming the clearance of Cupid by Zephyr2 in vivo.

EMBODIMENT OF CARRYING OUT THE INVENTION

Hereinafter, the present invention will be described in more detail.

(1) Clearing Agent

The compound of the present invention is a compound represented by the following formula (1) or a salt thereof, and is preferably a compound represented by the following formula (2), wherein n1 and n2 are 0:

[Formula 8]

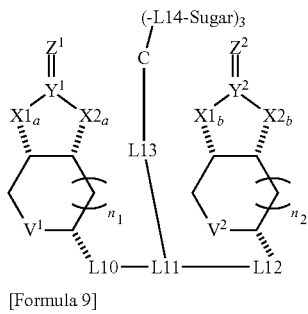
(1)

[Formula 9]

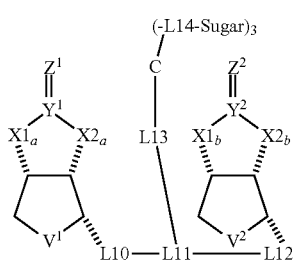
(2)

In the above formulae, X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; L10 and L12 each independently represent a divalent linking group; L11 represents a trivalent linking group; L14 represents a divalent linking group; and Sugar represents a sugar residue.

In the formula (1) and the formula (2), the moieties represented by the following structures:

[Formula 10]

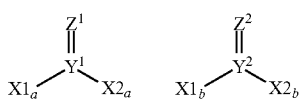

are preferably any one of the following formulae, but are not limited thereto:

[Formula 11]

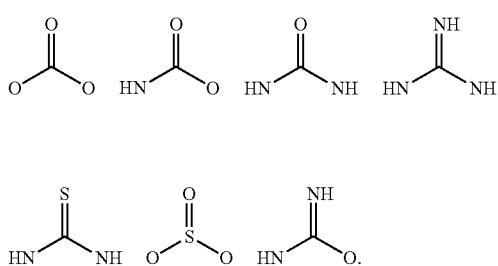

The compound of the present invention is preferably a compound represented by the following formula (3) or a salt thereof:

[Formula 12]

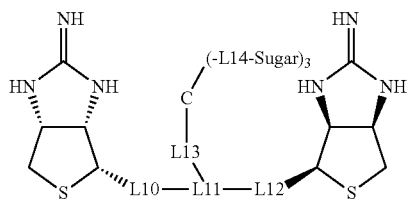
(3)

wherein L10, L12, L1, L14, and Sugar have the same meanings as above.

Preferably, L10 and L12 each independently represent an alkylene group containing 1 to 10 carbon atoms, —CONH—, —NHCO—, —O—, or a combination thereof. The alkylene group containing 1 to 10 carbon atoms may optionally have a substituent such as —COOCH$_3$.

More preferably, L10 and L12 each independently represent an alkylene group containing 1 to 5 carbon atoms, —CONH—, —NHCO—, or a combination thereof. The alkylene group containing 1 to 5 carbon atoms may optionally have a substituent such as —COOCH$_3$.

Even more preferably, L10 and L12 each independently represent a linking group consisting of a combination of two alkylene groups containing 1 to 5 carbon atoms and two —CONH—, or a linking group consisting of a combination of two alkylene groups containing 1 to 5 carbon atoms and two —NHCO—.

Further preferably, L10 and L12 each independently represent —(CH$_2$)$_p$—CONH—(CH$_2$)$_q$—CONH— or —NHCO—(CH$_2$)$_r$—NHCO—(CH$_2$)$_s$—. In the formulae, p, q, r and s each independently represent an integer from 1 to 10, preferably an integer from 1 to 6, more preferably an integer from 2 to 6, and further preferably 4 or 5.

Still further preferably, L10 and L12 each independently represent —(CH$_2$)$_p$—CONH—CH(COOCH$_3$)—(CH$_2$)$_q$—NHCO— or —CONH—(CH$_2$)$_r$—CH(COOCH$_3$)—NHCO—(CH$_2$)$_s$—. In the formulae, p, q, r and s each independently represent an integer from 1 to 10, preferably an integer from 1 to 6, more preferably an integer from 2 to 6, and further preferably 4 or 5.

L11 represents a trivalent linking group, and preferably a group represented by the following formula:

[Formula 13]

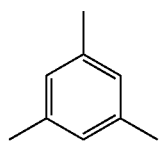

L13 preferably represents a linking group consisting of a combination of an alkylene group containing 1 to 10 carbon atoms, —CONH—, —NHCO—, —O—, and a group represented by the following formula:

[Formula 14]

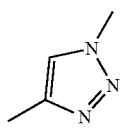

L14 preferably represents a linking group consisting of a combination of an alkylene group containing 1 to 10 carbon atoms, —CONH—, —NHCO—, and —O⁻.

Sugar represents a sugar residue. Examples of a preferred sugar residue may include, but are not particularly limited, residues such as glucose, mannose, galactose, N-acetylglucosamine, N-acetylmannosamine, and N-acetylgalactosamine.

Specific examples of the compound of the present invention may include the following compounds and salts thereof.

[Formula 15]

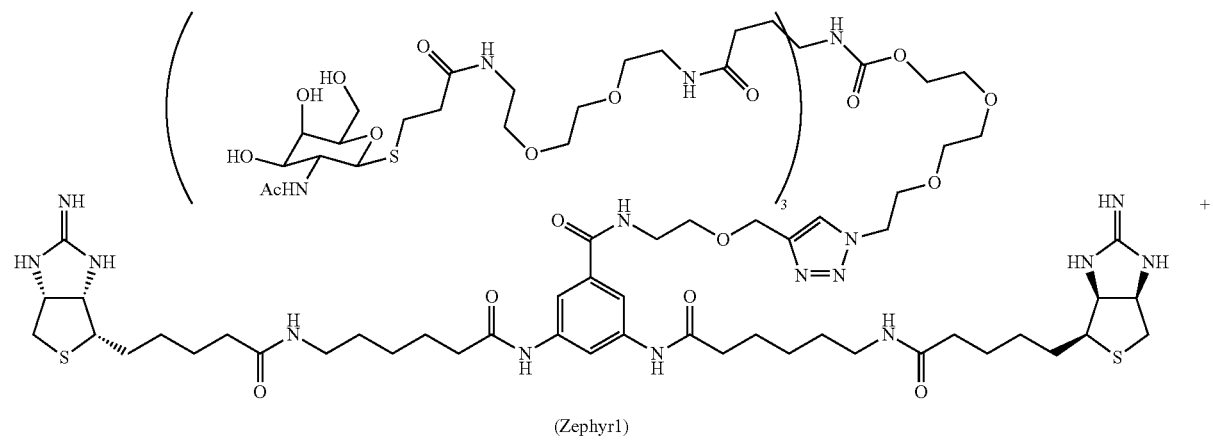

(Zephyr1)

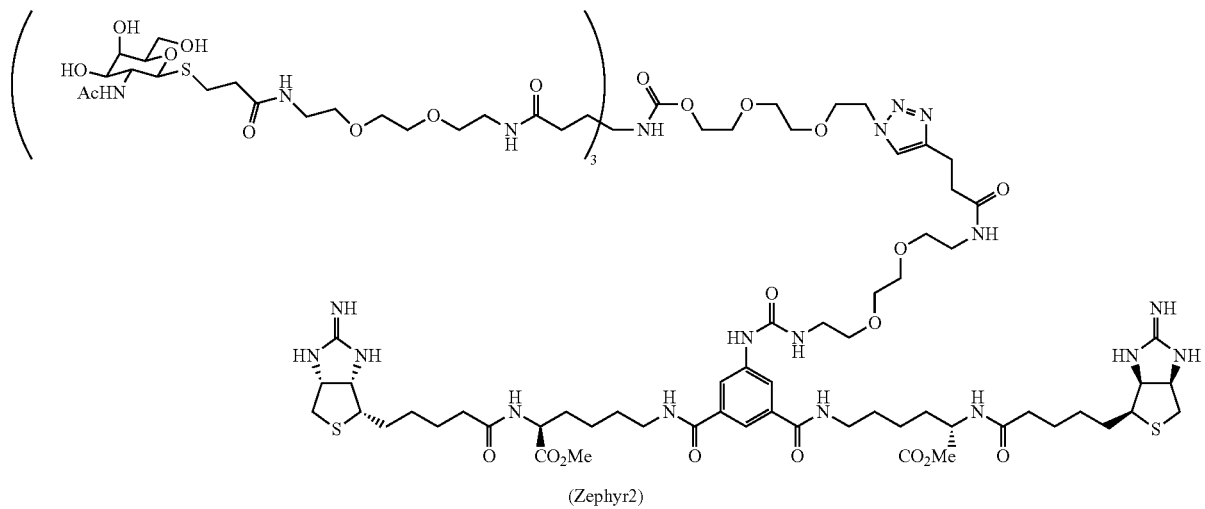

(Zephyr2)

The above-described compounds of the present invention (Compound 14 and Compound 25 shown in the after-mentioned Examples) can be synthesized by the synthesis method described in the after-mentioned Example 1 or a synthesis method equivalent thereto.

Synthesis of 3-(((2S,3R,4R,5R,6R)-3-acetamide-4, 5-diacetoxy-6-(acetoxymethyl)tetrahydro-2H-pyran-2-yl)thio)propionic Acid (Compound 2)

3-Mercaptopropionic acid and tin(IV) chloride are added to a dichloromethane solution of Compound 1, and the obtained mixture is then heated to reflux. The solvent is distilled away under reduced pressure, 0.1 N hydrochloric acid is then added to the residue, and the mixture is then extracted with ethyl acetate. The extract is dried over sodium sulfate, and the solvent is then distilled away under reduced pressure. The obtained crude product is purified by silica gel chromatography to obtain Compound 2.

Synthesis of (2R,3R,4R,5R,6S)-5-acetamide-2-(acetoxymethyl)-6-((3-((2,5-dioxopyrrolidin-1-yl)oxy)-3-oxopropyl)thio)tetrahydro-2H-pyran-3,4-diyl diacetate (Compound 3)

Acetonitrile is added to Compound 2, di(N-succinimidyl) carbonate is then added thereto. Thereafter, pyridine is added to the mixture, and the obtained mixture is stirred at room temperature. The solvent is distilled away under reduced pressure, and ethyl acetate is then added to the residue, and the obtained mixture is washed with a saturated sodium hydrogen carbonate aqueous solution and a saturated saline. The resultant is dried over sodium sulfate, and the solvent is then distilled away under reduced pressure. The obtained crude product is purified by neutral silica gel chromatography to obtain Compound 3.

Synthesis of di-tert-butyl (13-(2,2-dimethyl-4,15-dioxo-3,8,11-trioxa-5,14-diazaheptadecan-17-yl)-13-nitro-10,16-dioxo-3,6,20,23-tetraoxa-9,17-diazapentacosane-1,25-diyl)dicarbamate (Compound 5)

Dichloromethane is added to nitromethanetrispropionic acid, Amine 4, 1-ethyl-3-(3-dimethylaminopropyl)carbodiimide hydrochloride and 1-hydroxybenzotriazole-anhydrous, and thereafter, triethylamine is added thereto. The obtained mixture is stirred at room temperature. The solvent is distilled away under reduced pressure, ethyl acetate is then added to the residue, and the obtained mixture is then washed with 1 N hydrochloric acid, a saturated sodium hydrogen carbonate aqueous solution, and a saturated saline. An organic layer is dried over sodium sulfate, and is then distilled away under reduced pressure. The obtained crude product is purified by silica gel chromatography to obtain Compound 5.

Synthesis of di-tert-butyl (13-amino-13-(2,2-dimethyl-4,15-dioxo-3,8,11-trioxa-5,14-diazaheptadecan-17-yl)-10,16-dioxo-3,6,20,23-tetraoxa-9,17-diazapentacosane-1,25-diyl)dicarbamate (Compound 6)

Methanol is added to nickel(II) chloride, and sodium borohydride is then added thereto, The obtained mixture is stirred at room temperature. A methanol solution of Compound 5 is added to the reaction mixture, and sodium borohydride is gradually added thereto. The thus obtained mixture is stirred at room temperature, and is then filtrated with Celite. The obtained filtrate is distilled away under reduced pressure, and a saturated sodium hydrogen carbonate aqueous solution is then added thereto. The obtained mixture is extracted with ethyl acetate, is then washed with a saturated saline, and is then re-extracted with ethyl acetate and dichloromethane. An organic layer is dried over sodium sulfate, and is then distilled away under reduced pressure to obtain Compound 6.

Synthesis of 2,(2-(2-azidoethoxy)ethoxy)ethan-1-ol (Compound 8)

Sodium azide is added to an N,N-dimethylformamide solution of Alcohol 7, and the obtained mixture is then stirred at 80° C. Thereafter, distilled water is added to the reaction mixture, and the obtained mixture is then extracted with ethyl acetate and dichloromethane. An organic layer is dried over sodium sulfate, and is then distilled away under reduced pressure to obtain Compound 8.

Synthesis of 2-(2-(2-azidoethoxy)ethoxy)ethyl (2,5-dioxopyrrolidin-1-yl)carbonate (Compound 9)

Di(N-succinimidyl) carbonate is added to an N,N-dimethylformamide solution of Compound 8, and the obtained mixture is then stirred at room temperature. The solvent is distilled away under reduced pressure, ethyl acetate is then added thereto, and the obtained mixture is then washed with a saturated sodium hydrogen carbonate aqueous solution and a saturated saline. An organic layer is dried over sodium sulfate, and is then distilled away under reduced pressure to obtain Compound 9.

Synthesis of 2-(2-(2-azidoethoxy)ethoxy)ethyl di-tert-butyl (13-(2,2-dimethyl-4,15-dioxo-3,8,11-trioxa-5,14-diazaheptadecan-17-yl)-10,16-dioxo-3,6, 20,23-tetraoxa-9,17-diazapentacosane-1,13,25-triyl) tricarbamate (10)

A dichloromethane solution of Compound 6 is added to Compound 9, and triethylamine is then added thereto. The obtained mixture is stirred at 40° C. The solvent is distilled away under reduced pressure, ethyl acetate is then added thereto, and the obtained mixture is then washed with 1 N hydrochloric acid, a saturated sodium hydrogen carbonate aqueous solution, and a saturated saline. An organic layer is dried over sodium sulfate, and is then distilled away under reduced pressure. The obtained crude product is purified by silica gel chromatography to obtain Compound 10.

Synthesis of 13-(3-((2-(2-(2-(2-ammonioethoxy) ethoxy ethyl)amino)-3-oxopropyl)-13-(((2-(2-(2-azidoethoxy)ethoxy)ethoxy)carbonyl)amino)-10,16-dioxo-3,6,20,23-tetraoxa-9,17-diazapentacosane-1, 25-diammonium tri(2,2,2-trifluoroacetate) (11)

Trifluoroacetic acid is added to a dichloromethane solution of Compound 10. The obtained mixture is stirred at room temperature, and the solvent is then distilled away under reduced pressure to obtain a crude product (red oily product) containing Compound 11.

Synthesis of 2-(2-(2-azidoxethoxy)ethoxy)ethyl(1, 33-bis(((2S,3R,4R,5R6R)-3-acetamide-4,5-dihydroxy-6-(hydroxymethyl)tetrahydro-2H-pyran-2-yl) thio)-17-(16-(((2S,3R,4R,5R,6R)-3-acetamide-4,5-dihydroxy-6-(hydroxymethyl)tetrahydro-2H-pyran-2-yl)thio)-3,14-dioxo-7,10-dioxa-4,13-diazahexadecyl)-3,14,20,31-tetraoxo-7,10,24,27-tetraoxa-4,13,21,30-tetraazatritriacontan-17-yl) carbamate (12)

An N,N-dimethylformamide solution of Ammonium Salt 11 (12 mg, 10 μmol) is added to Succinimide 3 and 1-hydroxybenzotriazole-anhydrous, and N,N-diisopropylethylamine is then added thereto. The obtained mixture is stirred at room temperature, and the solvent is then distilled away under reduced pressure. Succinimide 3 is removed by silica gel chromatography, followed by eluting with methanol. To the obtained mixture, sodium methoxide is added, and the thus obtained mixture is then dissolved in methanol. The obtained solution is stirred at room temperature for 3 hours, and the solvent is then distilled away under reduced pressure. The obtained crude product is purified by reverse phase silica gel chromatography to obtain Compound 12.

Synthesis of (3aS,3a'S,4S,4'S,6aR,6a'R)-4,4'-(((((5-((2-((1-(28-(((2S,3R,4R,5R,6R)-3-acetamide-4,5-dihydroxy-6-(hydroxymethyl)tetrahydro-2H-pyran-2-yl)thio)-12,12-bis(16-(((2S,3R,4R,5R,6R)-3-acetamide-4,5-dihydroxy-6-(hydroxymethyl) tetrahydro-2H-pyran-2-yl)thio)-3,14-dioxo-7,10-dioxa-4,13-diazahexadecyl)-10,15,26-trioxo-3,6,9, 19,22-pentaoxa-11,16,25-triazaoctacosyl)-1H-1,2,3-triazol-4-yl)methoxy)ethyl)carbamoyl)-1,3-phenylene)bis(azanediyl))bis(6-oxohexane-6,1-diyl)) bis(azanediyl))bis(5-oxo pentane-5,1-diyl))bis (tetrahydro-1H-thieno[3,4-d]imidazol-2(3H)-iminium)di(2,2,2-trifluoroacetate) (14)

Compound 12 is added to Bisiminobiotin 13, and thereafter, copper sulfate pentahydrate, tris[(1-benzyl-1H-1,2,3-triazol-4-yl)methyl]amine, and sodium ascorbate are added thereto. Thereafter, distilled water and tert-butanol are added to the mixture. The obtained mixture is stirred at room temperature, and the solvent is then distilled away under reduced pressure. The obtained crude product is purified by reverse phase HPLC to obtain Compound 14.

Synthesis of dimethyl 6,6'-((5-(3-(2-(2-(2-(pent-4-ynamide)ethoxy)ethyl)ureido)isophthaloyl)bis (azanediyl))(2S,2'S)-bis(2-(5-((3 aS,4S,6aR)-2-iminohexahydro-1H-thieno[3,4-d]imidazol-4-yl) pentanamide)hexanoate) di(2,2,2-trifluoroacetate) (23)

N,N-Dimethylformamide and triethylamine are added to Bisiminobiotin 21 and N-Hydroxy Succinimidyl Ester 22. The obtained mixture is stirred at room temperature, and the solvent is then distilled away under reduced pressure. The obtained crude product is purified using automated purification equipment to obtain Compound 23.

Synthesis of dimethyl 6,6'-((5-(3-(2-(2-(2-(3-(1-(28-(((2S,3R,4R,5R,6R,)-acetamide-4,5-dihydroxy-6-(hydroxymethyl)tetra hydro-2H-pyran-2-yl)thio)-12,12-bis(16-(((2S,3R,4R,5R,6R)-3-acetamide-4,5-dihydroxy-6-(hydroxymethyl)tetrahydro-2H-pyran-2-yl)thio)-3,14-dioxo-7,10-dioxa-4,13-diazahexadecyl)-10,15,26-trioxo-3,6,9,19,22-pentaoxa-11,16,25-triazaoctacosyl)-1H-1,2,3-triazol-4-yl)propanamide)ethoxy)ethoxy)ureido) isophthaloyl)bis(azanediyl))(2S,2'S)-bis(2-(5-((3 aS,4S,6aR)-2-iminohexahydro-1H-thieno[3,4-d] imidazol-4-yl)pentanamide)hexanoate) di(2,2,2-trifluoroacetate) (25)

Compound 24 (the same as Compound 12) is added to Bisiminobiotin 23, and thereafter, copper sulfate pentahydrate ($CuSO_4 \cdot 5H_2O$), tris[(1-benzyl-1H-1,2,3-triazol-4-yl) methyl]amine (TBTA), and sodium ascorbate are added thereto. Thereafter, distilled water and acetonitrile are added to the mixture. The obtained mixture is stirred at room temperature, and the solvent is then distilled away under reduced pressure. The obtained crude product is purified by reverse phase HPLC to obtain Compound 25.

The above-described compound represented by the formula (1), formula (2) or formula (3) of the present invention, or a salt thereof, can be used as a clearing agent for clearing a fusion of a streptavidin mutant and a molecular probe.

(12) Therapeutic, In Vivo Diagnostic, or Ex Vivo Diagnostic Kit

The therapeutic, in vivo diagnostic, or ex vivo diagnostic kit according to the present invention comprises, at least, the above-described compound represented by the formula (1), formula (2) or formula (3) of the present invention, or a salt thereof, and a fusion of a streptavidin mutant and a molecular probe.

The streptavidin mutant of the present invention is preferably a streptavidin mutant consisting of the amino acid sequence as set forth in SEQ ID NO: 3, in which the amino acid residue at position 37, Asn, is substituted with another amino acid residue.

The streptavidin mutant of the present invention is particularly preferably a streptavidin mutant consisting of the amino acid sequence as set forth in SEQ ID NO: 4.

A protein having the amino acid sequence as set forth in SEQ ID NO: 3 has an amino acid sequence comprising the following mutations in a wild-type (natural) core streptavidin:

(1) a mutation, in which the amino acid residue at position 10, tyrosine, is substituted with serine;
(2) a mutation, in which the amino acid residue at position 71, tyrosine, is substituted with serine;
(3) a mutation, in which the amino acid residue at position 72, arginine, is substituted with lysine;
(4) a mutation, in which the amino acid residue at position 89, glutamic acid, is substituted with aspartic acid;
(5) a mutation, in which the amino acid residue at position 91, arginine, is substituted with lysine;
(6) a mutation, in which the amino acid residue at position 104, glutamic acid, is substituted with asparagine;
(7) a mutation, in which the amino acid residue at position 11, asparagine, is substituted with aspartic acid;
(8) a mutation, in which the amino acid residue at position 15, serine, is substituted with aspartic acid; and
(9) a mutation, in which the amino acid residue at position 33, serine, is substituted with asparagine.

The amino acid sequence as set forth in SEQ ID NO: 4 further has the following mutation in the amino acid sequence as set forth in SEQ ID NO: 3:
(10) a mutation, in which the amino acid residue at position 37, asparagine, is substituted with glycine.

In order to produce the streptavidin mutant used in the present invention, DNA encoding the streptavidin mutant is incorporated into an expression vector, and a host is then transformed with this expression vector, so that the streptavidin mutant of the present invention can be expressed.

When E. coli is used as a host, a vector preferably has a replication origin (ori) and further has a gene for selecting the transformed host (e.g., a drug resistance gene against drugs such as ampicillin, tetracycline, kanamycin, chloramphenicol, etc.). In addition, the expression vector used herein preferably has a promoter capable of efficiently expressing a streptavidin mutant in a host, such as a lacZ promoter or a T7 promoter. Examples of such a vector may include an M13 vector, a pUC vector, pBR322, pBluescript, pCR-Script, pGEX-5X-1 (Pharmacia), "QIAexpress system" (Qiagen), pEGFP, and pET (in this case, BL21 that expresses T7 RNA polymerase is preferably used as a host). Moreover, a signal sequence for increasing the yield of the streptavidin mutant, and the like, can be added to such a vector.

The vector can be introduced into host cells, for example, according to a calcium chloride method or an electroporation method. Moreover, a tag for improving solubility, such as, for example, a sequence encoding glutathione-S-transferase, thioredoxin or maltose-binding protein may also be added to the vector. Furthermore, a tag designed to facilitate purification, such as, for example, a polyhistidine tag, an Myc epitope, a hemagglutinin (HA) epitope, a T7 epitope, an Xpress tag, a FLAG peptide tag, or sequences encoding other known tag sequences, may also be added to the vector.

Examples of the expression vector other than E. coli may include mammal-derived expression vectors (e.g., pcDNA3 (manufactured by Invitrogen), pEGF-BOS (Nucleic Acids. Res. 1990, 18(17), p 5322), pEF, and pCDM8), insect cell-derived expression vectors (e.g., "Bac-to-BAC baculovairus expression system" (manufactured by Gibco BRL) and pBacPAK8), plant-derived expression vectors (e.g., pMH1 and pMH2), animal virus-derived expression vectors (e.g., pHSV, pMV, and pAdexLcw), retrovirus-derived expression vectors (e.g., pZIPneo), yeast-derived expression vectors (e.g., "Pichia Expression Kit" (manufactured by Invitrogen), pNV11, and SP-Q01), and Bacillus subtilis-derived expression vectors (e.g., pPL608 and pKTH50).

For the expression in animal cells such as CHO cells, COS cells, and NIH3T3 cells, the expression vector essentially has a promoter necessary for the expression in the cells, such as, for example, an SV40 promoter (Mulligan et al., Nature (1979) 277, 108), an MMLV-LTR promoter, an EF1α promoter (Mizushima et al., Nucleic Acids Res. (1990) 18, 5322), or a CMV promoter. It is more preferable, if the expression vector has a gene for selecting the transformation of cells (e.g., a drug resistance gene capable of determining the transformation of cells with a drug (neomycin, G418, etc.)). Examples of a vector having such properties may include pMAM, pDR2, pBK-RSV, pBK-CMV, pOPRSV, and pOP13.

Host cells, into which the vector is to be introduced, are not particularly limited. Either prokaryotes or eukaryotes may be used. For example, E. coli, various animal cells, and the like can be used.

In the case of using eukaryotes, for example, animal cells, plant cells, or fungal cells can be used as hosts. Examples of the animal cells that can be used herein include: mammalian cells such as CHO cells, COS cells, 3T3 cells, HeLa cells, or Vero cells; and insect cells such as Sf9, Sf21, or Tn5. When large-scale expression in animal cells is intended, the animal cells are particularly preferably CHO cells. The vector can be introduced into host cells, for example, according to a calcium phosphate method, a DEAE dextran method, a method using cationic liposome DOTAP (manufactured by Boehringer Mannheim), an electroporation method, or a lipofection method.

With regard to the plant cells that can be used herein, for example, Nicotiana tabacum-derived cells have been known as a protein production system, and these cells may be used in a callus culture. Examples of the known fungal cells include: yeasts, for example, genus Saccharomyces, such as Saccharomyces cerevisiae; and filamentous fungi, for example, genus Aspergillus, such as Aspergillus niger.

In the case of using prokaryotes, for example, Escherichia coli (E. coli), such as JM109, DH5α, or HB101 can be used. Other than these, Bacillus subtilis has been known.

The aforementioned cells are transformed with the DNA of the present invention, and the transformed cells are then cultured in vitro, to obtain the streptavidin mutant of the present invention. The culture can be carried out according to a known method. For example, as a culture medium for animal cells, DMEM, MEM, RPMI1640, or IMDM can be used. At that time, a serum replacement such as fetal calf serum (FCS) may be used in combination, or a serum-free culture may also be carried out. The pH is preferably approximately pH 6 to 8 during the culture. The culture is generally carried out at a temperature of approximately 30° C. to 40° C. for about 15 to 200 hours. Medium replacement, ventilation and stirring may be added to the culture, as necessary. In addition, growth factors may be added to promote proliferation of cells.

The streptavidin mutant can be used by binding it to a molecular probe. Examples of the molecular probe may include antibodies, peptides, nucleic acids, and aptamers. Specific examples of the molecular probe that can be used herein may include antibodies, peptides, nucleic acids, and aptamers, which target the following antigens that are specifically expressed in cancer:

Epiregulin, ROBO1,2,3,4,1-40-β-amyloid, 4-1BB, 5AC, 5T4, ACVR2B, an adenocarcinoma antigen, α-fetoprotein, angiopoietin 2, anthrax toxin, AOC3 (VAP-1), B-lymphoma cells, B7-H3, BAFF, β amyloid, a C242 antigen, C5, CA-125, carbonic anhydrase 9 (CA-IX), cardiac myosin, CCL11 (eotaxin-1), CCR4, CCR5, CD11, CD18, CD125, CD140a, CD147 (basigin), CD147 (basigin), CD15, CD152, CD154 (CD40L), CD154, CD19, CD2, CD20, CD200, CD22, CD221, CD23 (IgE receptor), CD25 (IL-2 receptor a chain), CD28, CD3, CD30 (TNFRSF8), CD33, CD37, CD38 (cyclic ADP ribose hydrolase), CD4, CD40, CD41 (integrin α-IIb), CD44 v6, CD5, CD51, CD52, CD56, CD6, CD70, CD74, CD79B, CD80, CEA, CFD, ch4D5, CLDN18.2, Clostridium difficile, clumping factor A, CSF2, CTLA-4, cytomegalovirus, cytomegalovirus glycoprotein B, DLL4, DR5, E. coli Shiga toxin type 1, E. coli Shiga toxin type 2, EGFL7, EGFR, endotoxin, EpCAM, episialin, ERBB3, E. coli (Escherichia coli), respiratory syncytial virus F protein, FAP, fibrin II 3 chain, fibronectin extra domain-B, folate receptor 1, Frizzled receptor, GD2, GD3 ganglioside, GMCSF receptor a chain, GPNMB, a hepatitis B surface antigen, hepatitis B virus, HER1, HER2/neu, HER3, HGF, HIV-1, HLA-DR3, HNGF, Hsp90, human β amyloid, human scatter factor receptor kinase, human TNF, ICAM-1 (CD54), IFN-α, IFN-γ, IgE, IgE Fc region, IGF-1 receptor, IGF-1, IgG4, IGHE, IL-1β, IL-12, IL-13, IL-17, IL-17A, IL-22, IL-23, IL-4, IL-5, IL-6, IL-6 receptor, IL-9, ILGF2, influenza A hemagglutinin, insulin-like growth factor I receptor, integrin α4, integrin α4β7, integrin α5β1, integrin α7β7, integrin αIIbβ3, integrin αvβ3, an integrin γ inducible protein, an interferon receptor, an interferon α/β receptor, ITGA2, ITGB2 (CD18), KIR2D, L-selectin (CD62L), Lewis-Y antigen, LFA-1 (CD11a), lipoteichoic acid, LOXL2, LTA, MCP-1, mesothelin, MS4A1, MUC1, mucin CanAg, myostatin, N-Glycolylneuraminic acid, NARP-1, NCA-90 (granulocyte antigen), NGF, NOGO-A, NRP1, *Olyctolagus cuniculus*, OX-40, oxLDL, PCSK9, PD-1, PDCD1, PDGF-Rα, phosphatidylserine, prostate cancer cells, *Pseudomonas aeruginosa*, a rabies virus glycoprotein, RANKL, respiratory syncytial virus, RHD, an Rh (Rhesus) factor, RON, RTN4, sclerostin, SDC1, selectinP, SLAMF7, SOST, sphingosine-1-phosphate, TAG-72, TEM1, tenascin C, TFβ1, TGFβ1, TGFβ2, TGF-β, TNF-α, TRAIL-R1, TRAIL-R2, tumor antigen CTAA16.88, tumor-spec glycosylation of MUC1, TWEAK receptor, TYRP1 (glycoprotein 75), VEGF-A, VEGFR-1, VEGFR2, vimentin, and VWF.

Specific examples of a preferred molecular probe may include anti-human CD20 antibodies (e.g., Rituximab) and anti-epiregulin single chain antibodies. Rituximab is an anti-human CD20 antibody, and human CD20 is only expressed in human B cells. A therapeutic agent for cell non-Hodgkin's lymphoma and mantle cell lymphoma, which is prepared by labeling a mouse-type anti-CD20 monoclonal antibody with radioisotope 90Y, is commercially available with the name Zevalin (registered trademark). In this pharmaceutical product, an anti-CD20 antibody is directly labeled with RI, and several days are required for accumulation thereof in tumor after administration of the product into a body. As such, severe side effects, such as bone marrow suppression, are caused by RI. For solving these problems, a pretargeting method has been proposed. Pagneli et al. have studied a pretargeting method, in which a fusion protein of an anti-CD20 antibody-scfv and a streptavidin mutant, and RI-labeled biotin or bisbiotin are used.

Epiregulin is a member of epidermal growth factors, and has been known to function as a cancer growth inhibitory factor that induces a morphological change to Hela cells. Aburatani et al. have produced an anti-epireulin antibody (WO 2008/047723). On the other hand, Lee et al. have conducted humanization of an anti-epiregulin antibody and evaluation thereof (Biochemical and Biophysical Research communications 444 (2013) 1011-1017).

That is to say, a fusion of a molecular probe such as a cancer antigen-specific antibody molecule and a streptavidin mutant is prepared, and it is then administered to a patient, so that the streptavidin mutant specific to cancer cells can be accumulated in the body of the patient. Thereafter, a diagnostic or therapeutic substance that binds to a biotin variant having an affinity to the above-described streptavidin mutant (e.g., a fluorescent dye, a chemiluminescent agent, a radio-isotope, a sensitizer consisting of a metal compound or the like, a neutron capturing agent consisting of a metal compound or the like, a low molecular weight compound such as a drug, micro- or nano-bubbles, a protein, etc.) is administered to a patient, so that it becomes possible to allow the substance to accurately accumulate in cancer cells.

In the present invention, a fusion of a molecular probe and a streptavidin mutant is administered to a patient, and the clearing agent of the present invention is then administered to the patient, so that the above-described fusion, which does not specifically accumulate in cancer cells but remains in the body, can be promptly remove (clear) from the body. Thereby, the diagnostic or therapeutic substance can be prevented from being non-specifically accumulated in the body, and pseudo-positive results in the diagnosis and side effects generated in the treatment can be reduced.

Various types of molecules can be used as antibodies to be bound to the streptavidin mutant. Either a polyclonal antibody or a monoclonal antibody can be used. The subclass of such an antibody is not particularly limited, but preferably IgG, and particularly preferably $IgG_1$ is used. In addition, the term "antibody" includes all of modified antibodies and antibody fragments. Examples of the antibody used herein may include a humanized antibody, a human-type antibody, a human antibody, antibodies derived from various types of animals such as a mouse, a rabbit, a rat, a Guinea pig and a monkey, chimeric antibodies of human antibodies and antibodies derived from various types of animals, diabody, scFv, Fd, Fab, Fab', and F(ab)'$_2$, but the examples are not limited thereto.

Such a fusion of a streptavidin mutant and an antibody can be obtained by using a method known to a person skilled in the art. For example, the fusion can be obtained by a chemical bond method (U.S. Pat. No. 5,608,060), or can also be obtained in the form of a fusion protein by connecting DNA encoding a streptavidin mutant with DNA encoding an antibody, and then allowing it to express in host cells using an expression vector or the like. The DNA encoding a streptavidin mutant may be connected with the DNA encoding an antibody, via DNA encoding a suitable peptide called a linker. Such a streptavidin mutant-antibody fusion is desirably produced, while maintaining a specific bonding power between an antibody and a target molecule.

The kit of the present invention may further comprise a therapeutic, in vivo diagnostic, or ex vivo diagnostic substance, which is labeled with a compound represented by the following formula (10):

[Formula 16]

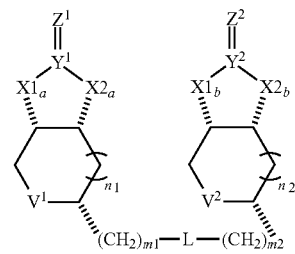

(10)

wherein X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; m1 and m2 each independently represent an integer from 1 to 10; and L represents a linking group.

The above-described compound represented by the formula (10) (hereinafter also referred to as a "dimeric compound of biotin variant") is described as a compound represented by formula (1) in International Publication No. WO 2015/125820. The content described in International Publication No. WO 2015/125820, in particular, the compound represented by the formula (1) in International Publication No. WO 2015/125820 and a preferred structure thereof are all cited in the description of the present application. As a compound represented by the above-described formula (10) in the present invention, the following specific compounds that are described in International Publication No. WO 2015/125820 can be used:

[Formula 17]
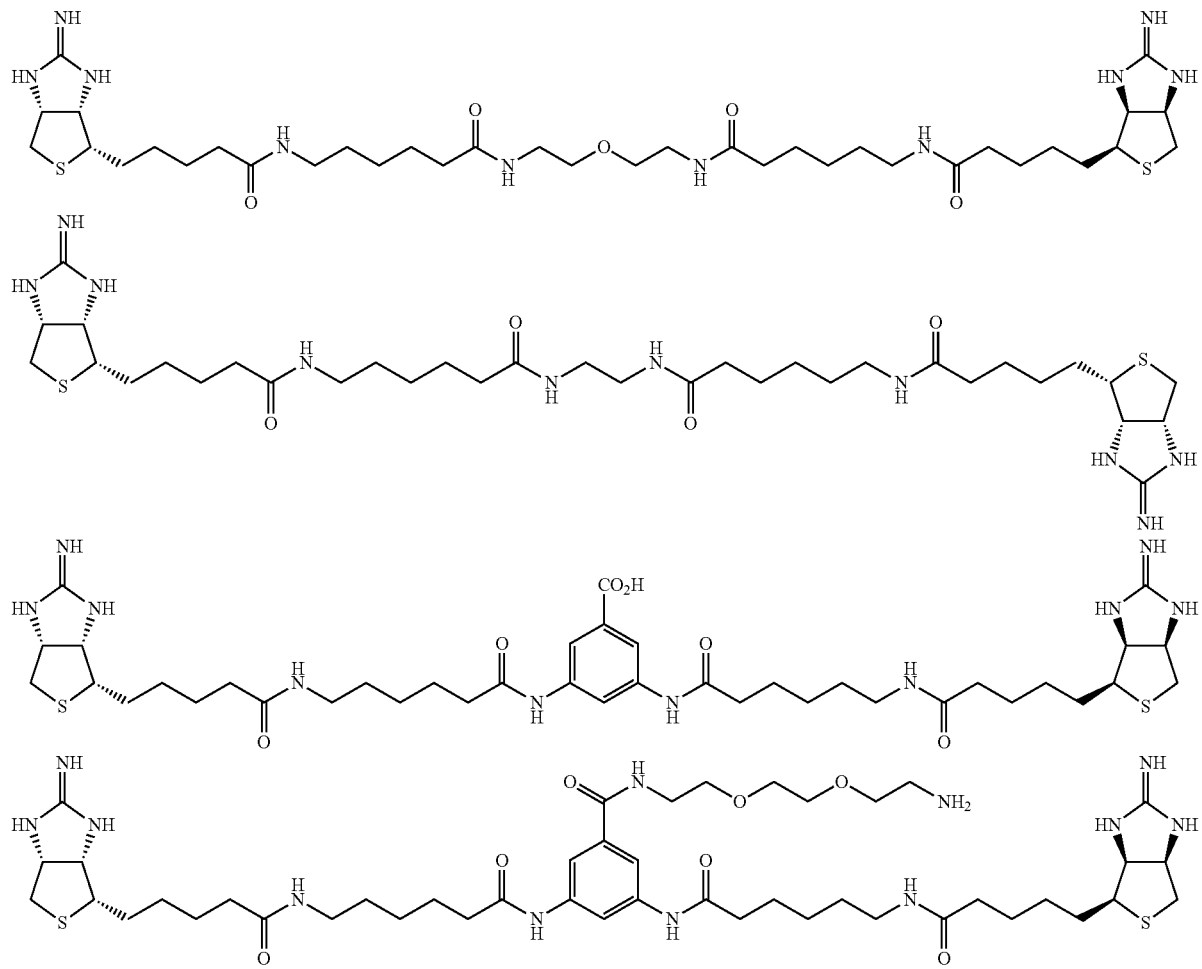
[Formula 18]
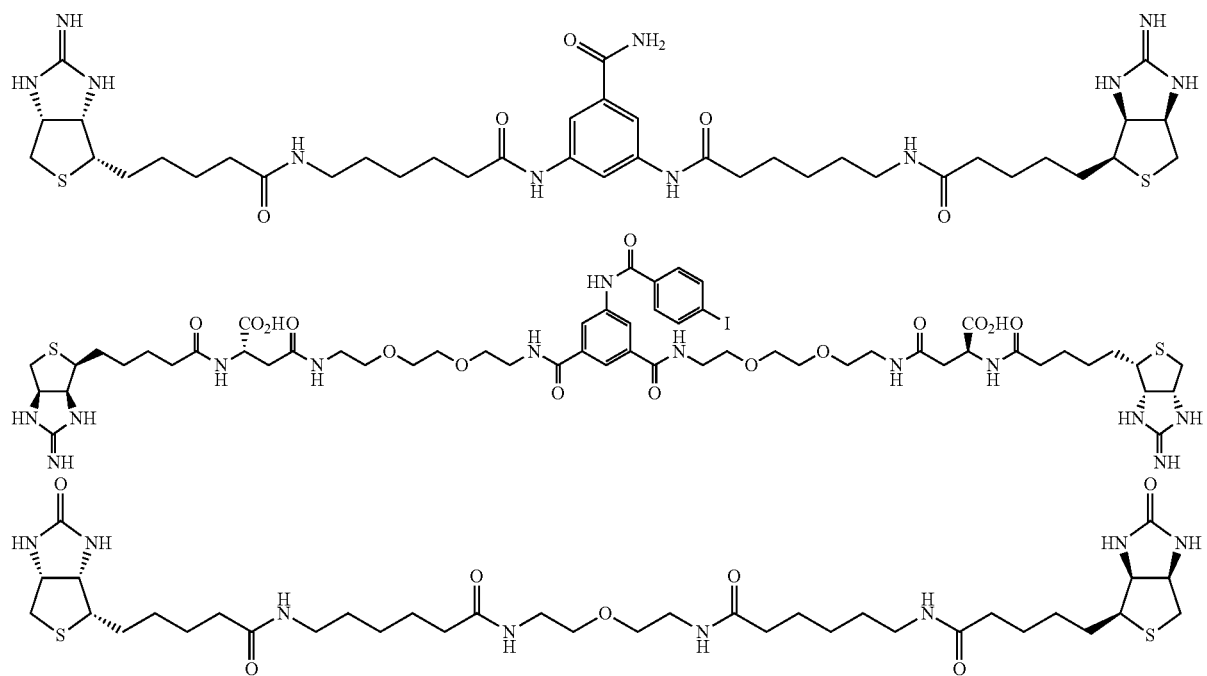

[Formula 19]
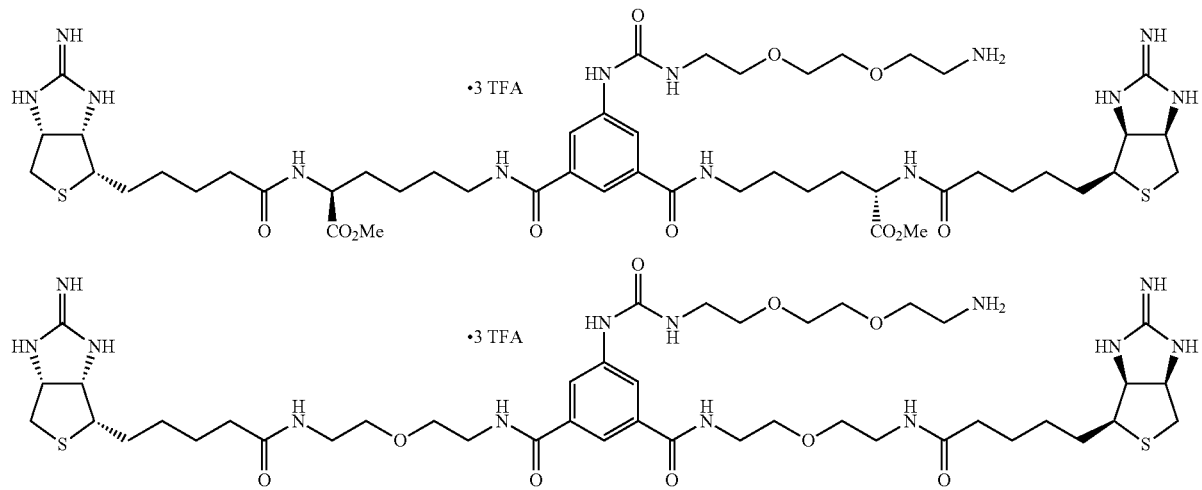
[Formula 20]
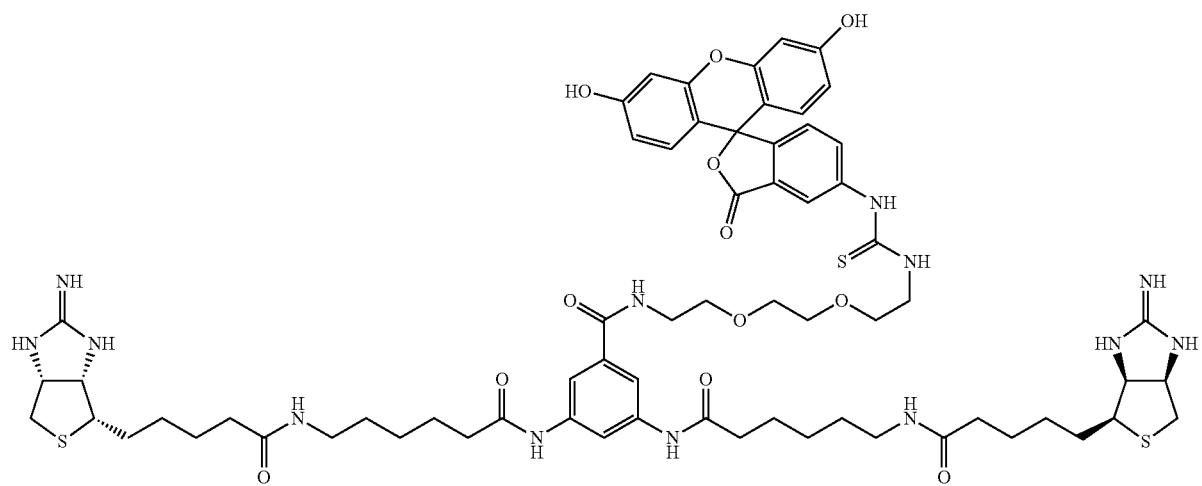
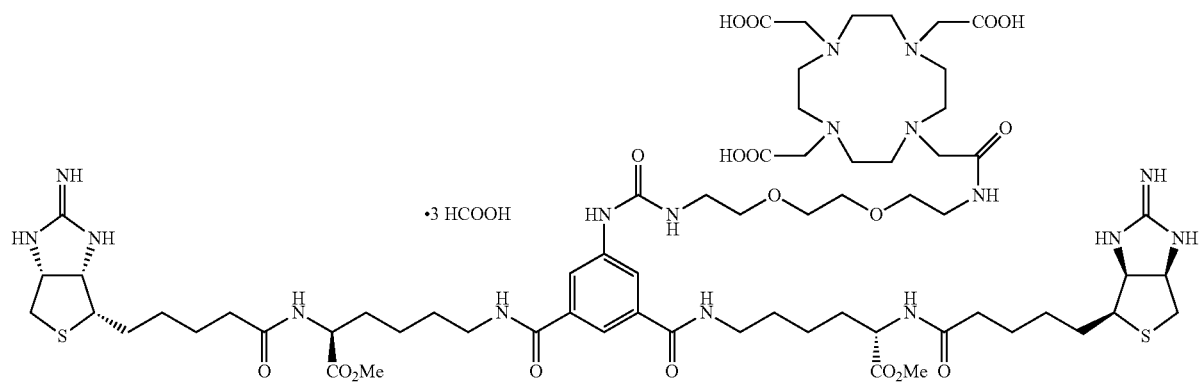

23 24
-continued
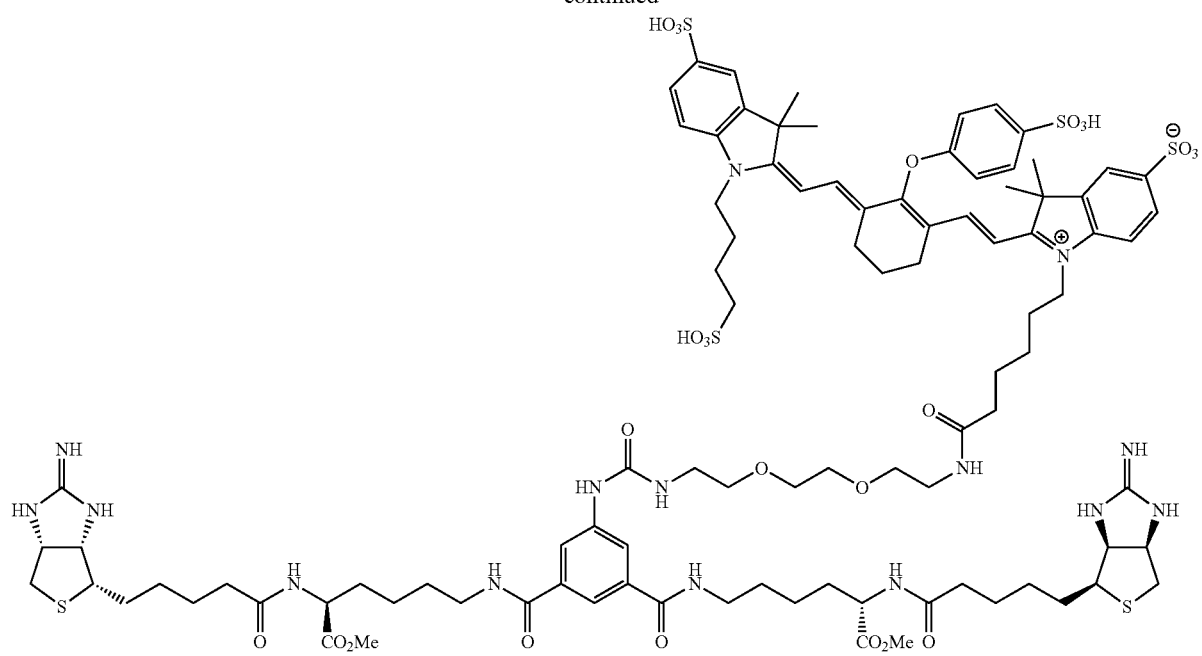
[Formula 21]
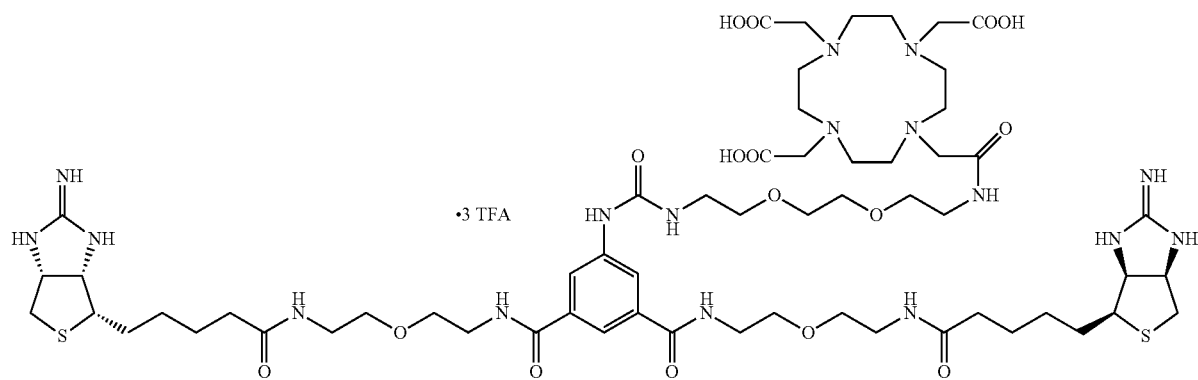
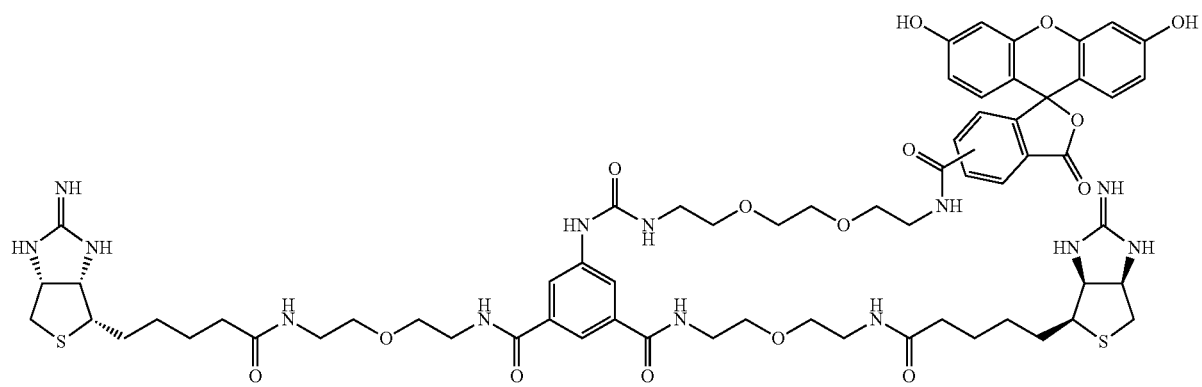

-continued

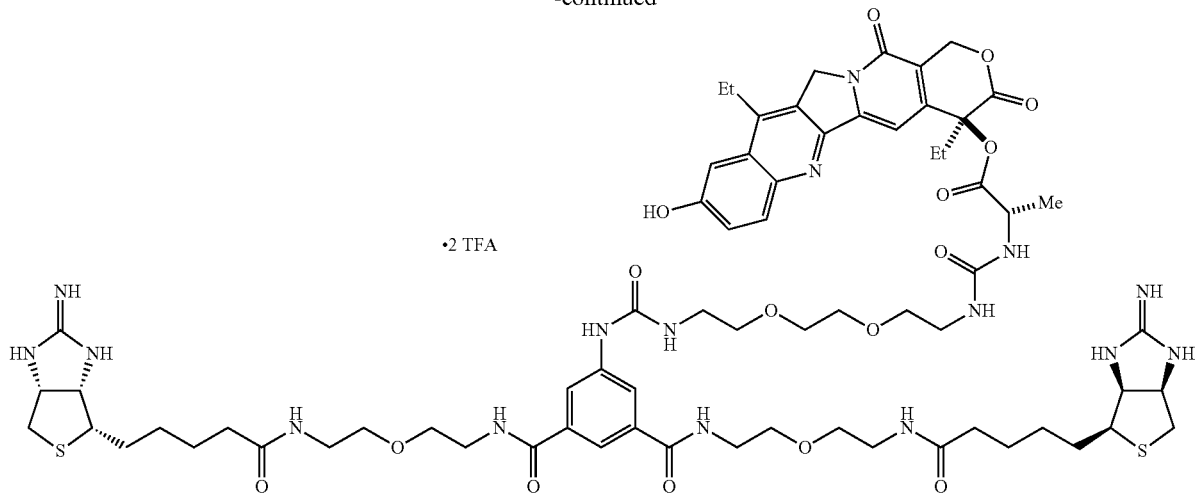

In the present invention, a therapeutic, in vivo diagnostic, or ex vivo diagnostic substance, which is labeled with the compound represented by the formula (10) (a dimeric compound of biotin variant), can be used.

When a radioisotope is used as such a therapeutic, in vivo diagnostic, or ex vivo diagnostic substance, the dimeric compound of biotin variant represented by the formula (10), to which a chelating group for capturing the radioisotope binds, may be used. Examples of such a chelating group may include DOTA (1,4,7,10-tetraazacyclododecane-N,N',N'',N'''-tetraacetic acid), DTPA (diethylenetriaminepentaacetic acid), TETA (1,4,8,11-tetraazacyclotetradecane-N,N',N'',N'''-tetraacetic acid), N2S2, MAG3, and CHX-A-DTPA.

A compound, in which a radioisotope is captured by the above-described chelating group-binding compound, can be provided. Among isotopes captured by the chelating group, as radioisotopes for imaging, gamma-emitting radionuclides ($^{67}Ga$, $^{99m}Tc$, $^{111}In$, and $^{123}I$) and positron-emitting radionuclides ($^{18}F$, $^{62}Cu$, $^{64}Cu$, $^{66}Ga$, $^{68}Ga$, $^{76}Br$, $^{86}Y$, $^{89}Zr$, $^{4}Tc$, and $^{124}I$) can be used. As therapeutic radioisotopes, beta-emitting radionuclides ($^{32}P$, $^{67}Cu$, $^{89}Sr$, $^{90}Y$, $^{114m}In$, $^{117m}Sn$, $^{131}I$, $^{153}Sm$, $^{166}Ho$, $^{177}Lu$, $^{186}Re$, $^{188}Re$, etc.), alpha-emitting radionuclides ($^{211}At$, $^{212}Bi$, $^{212}Pb$, $^{213}Bi$, $^{223}Ra$, $^{225}Ac$, etc.), and Auger electron-emitting radionuclides ($^{125}I$, $^{165}Er$, etc.) can be used. Among the above-described radioisotopes, $^{64}Cu$, $^{124}I$, $^{76}Br$, $^{68}Ga$, $^{99}Tc$, $^{123}I$, $^{131}I$, and $^{90}Y$ can be preferably used.

In the present invention, a compound, in which a fluorescent compound or a drug compound (e.g., an anticancer agent) binds to the above-described dimeric compound of biotin variant, can also be used.

Examples of the fluorescent compound that can be used in the present invention may include fluorescein-5-isothiocyanate (FITC), IR Dye (registered trademark) 800, and fluorescein. Examples of the drug that can be used in the present invention (e.g., an anticancer agent) may include PBD (pyrrolobenzodiazepine) classes (e.g., SJG-136, SG2202, etc.), maytansine analogs (e.g., DM1, DM4, etc.), dolastatin analogs (e.g., Monomethyl auristatin E (MMAE), monomethyl auristatin F (MMAF), dolastatin 10, tubulysin, etc.), duocarmycin analogs (e.g., DC1, DC4, DC44, etc.), camptothecin analogs (e.g., SN-38, etc.), and others (e.g., methotrexate, vinblastine, calicheamicin, α-amanitin, doxorubicin, and melphalan).

The present invention will be more specifically described in the following examples. However, these examples are not intended to limit the scope of the present invention.

EXAMPLES

Example 1: Synthesis of Clearing Agent (Compound 14)

Common Method

The nuclear magnetic resonance (NMR) spectrum was measured using JEOL ECX500 ($^1$H NMR: 500 MHz) or JEOL ECS400 ($^1$H NMR: 400 MHz) spectrometer. The chemical shift was shown in the form of a ppm value with respect to the solvent peak remaining in a deuterated solvent as an internal reference (CDCl$_3$: δ=7.26 ppm, CD$_3$OD: δ=3.31 ppm). The low resolution mass spectrum (LRMS) was measured using ESI-MS, employing Shimadzu Corporation LCMS-2020. Column chromatography was carried out using silica gel (Kanto Kagaku 60 (40 to 50 μm)), or silica gel (Kanto Kagaku 60N (40 to 100 μm)), or Wakosil® 40C18 (30 to 50 μm, 70+%). The reaction was traced by thin layer chromatography (TLC) or low resolution mass spectrometry (LRMS).

Reverse phase high performance liquid chromatography was carried out using JASCO-HPLC System. Detection was carried out using ultraviolet light at a wavelength of 210 nm or 254 nm, and a gradient solvent system (acetonitrile/0.1% trifluoroacetic acid MQ solution) was used as a mobile phase. For analysis, a YMC-Pack ODS-AM (150×4.6 mL) or YMC-Triart-C18 (150×4.6 mL) column was used, and a flow rate was set at 1 mL/min. For separation, a YMC-Triart-C18 (250×10 mL) column was used, and a flow rate was set at 3 mL/min.

Reagents were purchased from Aldrich, Tokyo Chemical Industry, Co., Ltd. (TCI), KANTO CHEMICAL CO., INC. (Kanto), Wako Pure Chemical Industries, Ltd., and WATANABE CHEMICAL INDUSTRIES, LTD. With regard to all reagents and solvents, commercially available products were directly used, unless otherwise specified.

3-(((2S,3R,4R,5R,6R)-3-Acetamide-4,5-diacetoxy-6-(acetoxymethyl)tetrahydro-2H-pyran-2-yl)thio)propionic Acid (Compound 2)

[Formula 22]

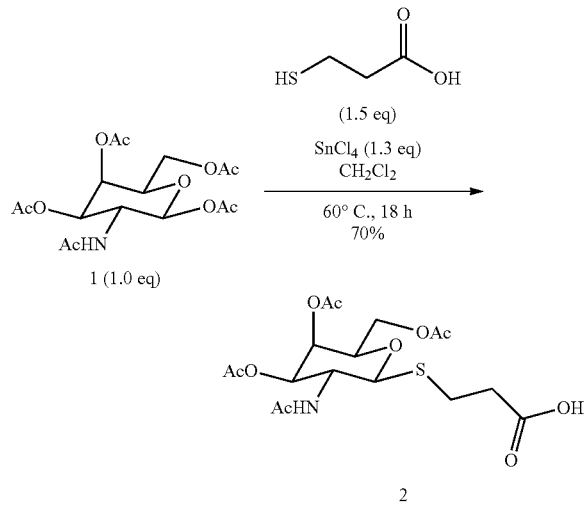

3-Mercaptopropionic acid (158 mg, 129 μL) and tin(IV) chloride (336 mg, 149 μL) were added to a dichloromethane (10 mL) solution of Compound 1 (386 mg, 0.99 mmol) that had been synthesized by a known method (Wang et al., Journal of Bacteriology, (2014), 196, 3122), and the obtained mixture was then heated to reflux at 60° C. for 18 hours. Thereafter, the solvent was distilled away under reduced pressure, 0.1 N hydrochloric acid was then added to the residue, and the obtained mixture was then extracted with ethyl acetate twice. The extract was dried over sodium sulfate, and the solvent was then distilled away under reduced pressure. The obtained crude product was purified by silica gel chromatography (dichloromethane/methanol=15:1, acetic acid 0.5%) to obtain Compound 2 (300 mg; yield: 70%; a white amorphous substance).

$^1$H NMR (500 MHz, CDCl$_3$) δ: 1.97 (s, 3H), 2.00 (s, 3H), 2.07 (s, 3H), 2.17 (s, 3H), 2.77 (ddd, 2H, J=6.9, 6.9, 2.3 Hz), 2.98 (ddd, 2H, J=6.9, 6.9, 2.3 Hz), 3.89 (t, 1H, J=5.8 Hz), 4.06 (dd, 1H, J=11.5, 6.9 Hz), 4.19-4.25 (m, 2H), 4.74 (d, 1H, J=10.3 Hz), 5.13 (dd, 1H, J=10.9, 3.5 Hz), 5.39 (d, 1H, J=3.5 Hz), 5.51 (d, 1H, J=9.2).

(2R,3R,4R,5R,6S)-5-Acetamide-2-(acetoxymethyl)-6-((3-((2,5-dioxopyrrolidin-1-yl)oxy)-3-oxopropyl)thio)tetrahydro-2H-pyran-3,4-diyl diacetate (Compound 3)

[Formula 23]

Acetonitrile (7.0 mL) was added to Carboxylic acid 2 (300 mg, 0.69 mmol), and di(N-succinimidyl) carbonate (265 mg, 1.0 mmol) was then added thereto. Thereafter, pyridine (164 mg, 167 μL, 2.1 mmol) was added to the mixture, and the obtained mixture was then stirred at room temperature for 17.5 hours. Thereafter, the solvent was distilled away under reduced pressure, ethyl acetate was then added to the residue, and the obtained mixture was then washed with a saturated sodium hydrogen carbonate aqueous solution once, and then with a saturated saline once. The resultant was dried over sodium sulfate, and the solvent was then distilled away under reduced pressure. The obtained crude product was purified by neutral silica gel chromatography (dichloromethane/methanol=30:1) to obtain the title Compound 3 (297 mg; yield: 80%; a white amorphous substance).

$^1$H NMR (500 MHz, CDCl$_3$) δ: 1.96 (s, 3H), 2.00 (s, 3H), 2.05 (s, 3H), 2.17 (s, 3H), 2.89-2.99 (m, 6H), 3.05-3.22 (m, 2H), 3.88-3.91 (dd, 1H, J=6.6, 6.6 Hz), 4.12 (dd, 1H, J=3.1, 6.6), 4.15 (dd, 1H, J=3.1, 6.6), 4.30 (q, 1H, J=10.3 Hz), 4.70-4.72 (d, 1H, J=10.3 Hz), 5.05 (dd, 1H, J=10.9, 3.5 Hz), 5.38 (d, 1H, J=3.5 Hz), 5.90 (d, 1H, J=9.8 Hz)

di-tert-Butyl (13-(2,2-dimethyl-4,15-dioxo-3,8,11-trioxa-5,14-diazaheptadecan-17-yl)-13-nitro-10,16-dioxo-3,6,20,23-tetraoxa-9,17-diazapentacosane-1,25-diyl)dicarbamate (Compound 5)

[Formula 24]

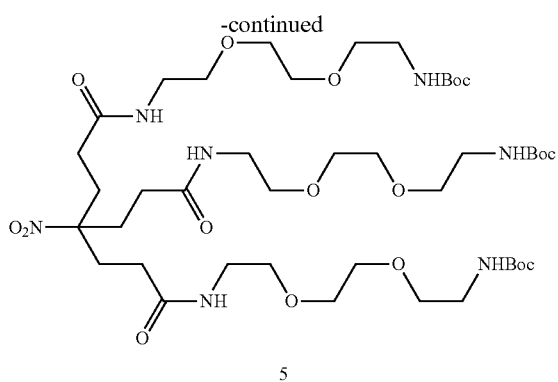

5

Dichloromethane (5.4 mL) was added to nitromethane-trispropionic acid (150 mg, 0.54 mmol), Amine 4 (436 mg, 1.8 mmol) synthesized by a known method (Wilbur et al., *Bioconjugate. Chem.* (2010) 21, 1225), 1-ethyl-3-(3-dimethylaminopropyl)carbodiimide hydrochloride (WSC·HCl, 363 mg, 1.9 mmol) and 1-hydroxybenzotriazole-anhydrous (HOBt anhydrous, 256 mg, 1.9 mmol), and thereafter, triethylamine (274 mg, 0.38 mL, 2.7 mmol) was added thereto. The obtained mixture was stirred at room temperature for 13.5 hours. Thereafter, the solvent was distilled away under reduced pressure, ethyl acetate was then added to the residue. The obtained mixture was washed with 1 N hydrochloric acid once, then with a saturated sodium hydrogen carbonate aqueous solution once, and then with a saturated saline once. An organic layer was dried over sodium sulfate, and was then distilled away under reduced pressure. The obtained crude product was purified by silica gel chromatography (dichloromethane/methanol=20:1) to obtain the title Compound 5 (412 mg; yield: 79%; a transparent oily substance).

$^1$H NMR (500 MHz, CDCl$_3$) δ: 1.42 (s, 27H), 2.16 (d, 6H, J=5.6 Hz), 2.24 (d, 6H, J=7.5 Hz), 3.29 (d, 6H, J=5.2 Hz), 3.42 (q, 6H, J=5.2 Hz), 3.51-3.55 (m, 24H), 5.12 (brs, 2H), 6.45 (brs, 2H).

di-tert-Butyl (13-amino-13-(2,2-dimethyl-4,15-dioxo-3,8,11-trioxa-5,14-diazaheptadecadecan-17-yl)-10,16-dioxo-3,6,20,23-tetraoxa-9,17-diazapentacosane-1,25-diyl)dicarbamate (Compound 6)

[Formula 25]

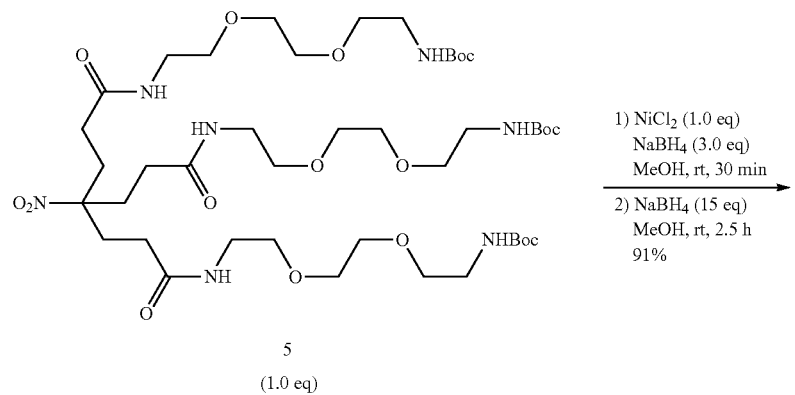

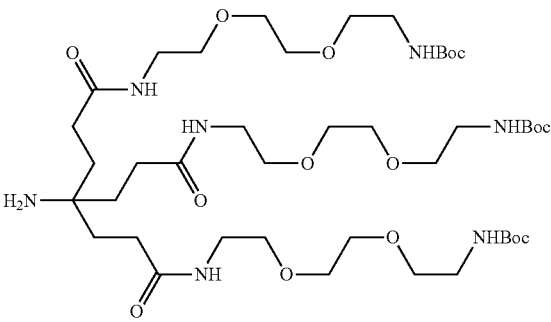

Methanol (4.0 mL) was added to nickel(II) chloride (36 mg, 0.28 mmol), and sodium borohydride (33 mg, 0.83 mmol) was then added thereto. The obtained mixture was stirred at room temperature for 30 minutes. Thereafter, a methanol (12 mL) solution of Compound 5 (269 mg, 0.28 mmol) was added to the reaction mixture, and sodium borohydride (166 mg, 4.2 mmol) was gradually added thereto. The thus obtained mixture was stirred at room temperature for 2.5 hours, and was then filtrated with Celite. The filtrate was distilled away under reduced pressure, and a saturated sodium hydrogen carbonate aqueous solution was then added thereto. The obtained mixture was extracted with ethyl acetate twice. The extract was washed with a saturated saline, and thereafter, the resultant was re-extracted with ethyl acetate once and then with dichloromethane once. An organic layer was dried over sodium sulfate, and was then distilled away under reduced pressure to obtain the title Compound 6 (237 mg; yield: 91%).

1H NMR (400 MHz, CDCl$_3$) δ: 1.42 (s, 27H), 1.67 (brs, 6H), 2.24 (brs, 6H), 3.29-3.31 (m, 6H), 3.42 (q, 6H, J=5.0 Hz), 3.53 (q, 12H, J=5.5 Hz), 3.59 (s, 12H), 5.24 (brs, 2H), 6.58 (brs, 2H).

2,(2-(2-Azidoethoxy)ethoxy)ethan-1-ol (Compound 8)

[Formula 26]

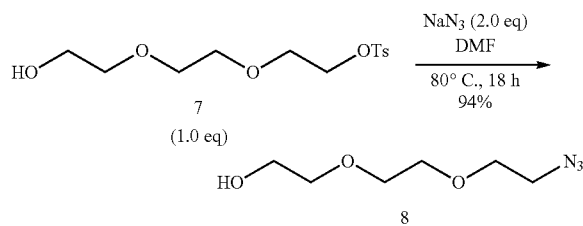

Sodium azide (1.78 g, 27 mmol) was added to an N,N-dimethylformamide (30 mL) solution of Alcohol 7 (4.15 g, 14 mmol), and the obtained mixture was then stirred at 80° C. for 18 hours. Thereafter, distilled water was added to the reaction mixture, and the thus obtained mixture was then extracted with ethyl acetate twice, and then with dichloromethane three times. An organic layer was dried over sodium sulfate, and was then distilled away under reduced pressure to obtain the title Compound 8 (2.26 g; yield: 94%; a yellowish brown oily substance).

$^1$H NMR (400 MHz, CDCl$_3$) δ: 2.36 (brs, 1H), 3.36 (t, 2H, J=5.3 Hz), 3.52-3.71 (m, 10H)

2-(2-(2-Azidoethoxy)ethoxy)ethyl(2,5-dioxopyrrolidin-1-yl)carbonate (Compound 9)

[Formula 27]

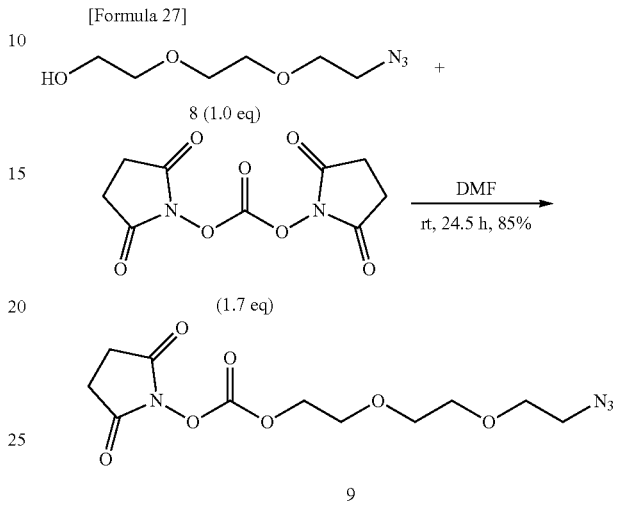

Di(N-succinimidyl) carbonate (1.2 g, 4.9 mmol) was added to an N,N-dimethylformamide (10 mL) solution of Alcohol 8 (514 mg, 2.9 mmol), and the obtained mixture was then stirred at room temperature for 24.5 hours. Thereafter, the solvent was distilled away under reduced pressure, ethyl acetate was then added to the residue, and the obtained mixture was then washed with a saturated sodium hydrogen carbonate aqueous solution once, and then with a saturated saline once. An organic layer was dried over sodium sulfate, and was then distilled away under reduced pressure to obtain the title Compound 9 (781 mg; yield: 85%; a yellowish brown oily substance).

$^1$H NMR (400 MHz, CDCl$_3$) δ: 2.83 (s, 4H), 3.39 (t, 2H, J=5.3 Hz), 3.66-3.70 (m, 6H), 3.78-3.80 (m, 2H), 4.45-4.48 (m, 2H).

2-(2-(2-Azidoethoxy)ethoxy)ethyl di-tert-butyl (13-(2,2-dimethyl-4,15-dioxo-3,8,11-trioxa-5,14-diazaheptadecan-7-yl)-10,16-dioxo-3,6,20,23-tetraoxa-9,17-diazapentacosane-1,13,25-triyl)tricarbamate (10)

[Formula 28]

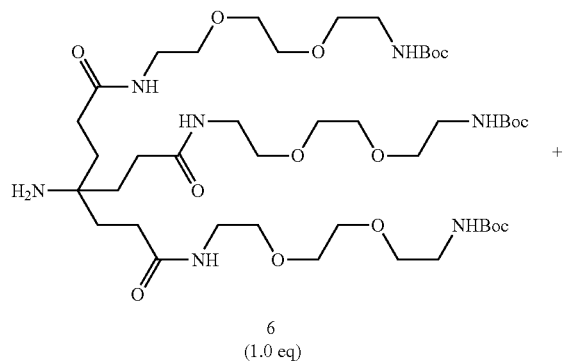

-continued

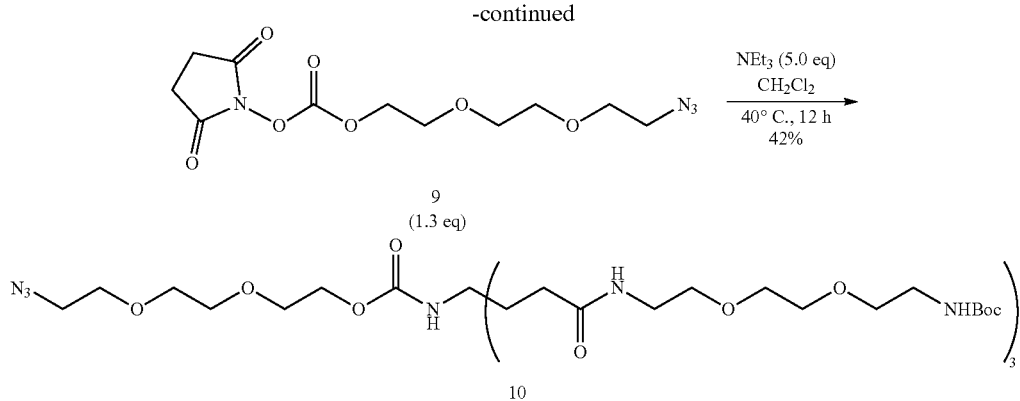

A dichloromethane (1.4 mL) solution of Amine 6 (100 mg, 0.11 mmol) was added to Compound 9 (44 mg, 0.14 mmol), and thereafter, triethylamine (NEt$_3$, 53 mg, 74 µL, 0.52 mmol) was added thereto. The obtained mixture was stirred at 40° C. for 12 hours. Thereafter, the solvent was distilled away under reduced pressure, and ethyl acetate was then added to the residue. The obtained mixture was washed with 1 N hydrochloric acid once, then with a saturated sodium hydrogen carbonate aqueous solution once, and then with a saturated saline once. An organic layer was dried over sodium sulfate, and was then distilled away under reduced pressure. The obtained crude product was purified by silica gel chromatography (dichloromethane/methanol=15:1→10:1) to obtain the title Compound 10 (51 mg; yield: 42%).

$^1$H NMR (400 MHz, CDCl$_3$) δ: 1.37 (s, 27H), 1.88-1.91 (m, 6H), 2.12-2.16 (m, 6H), 3.07 (s, 2H), 3.25-3.26 (d, 6H, J=5.0 Hz), 3.32-3.37 (m, 8H), 3.46-3.63 (m, 34H), 4.08 (brs, 2H), 5.22 (brs, 2H), 6.65 (brs, 2H).

13-(3-((2-(2-(2-(2-Ammonioethoxy)ethoxy)ethyl)amino)-3-oxopropyl)-13-(((2-(2-(2-azidoethoxy)ethoxy)ethoxy)carbonyl)amino)-10,16-dioxo-3,6,20,23-tetraoxa-9,17-diazapentacosane-1,25-diammonium tri(2,2,2-trifluoroacetate) (11)

[Formula 29]

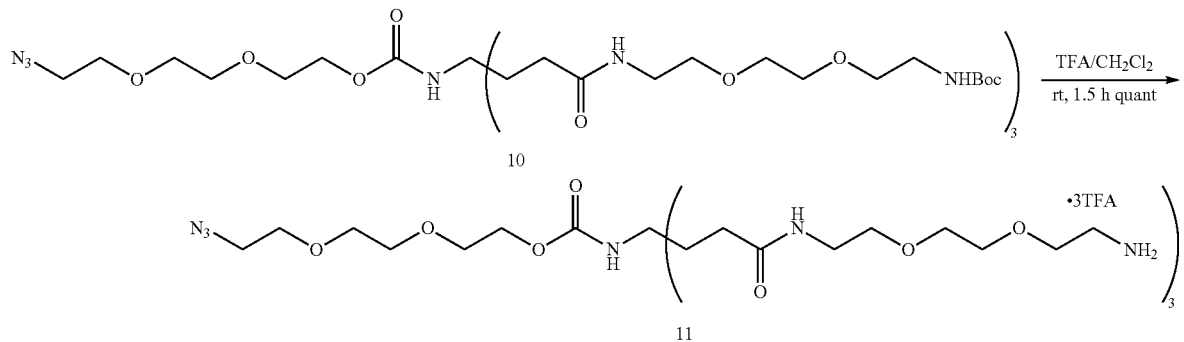

Trifluoroacetic acid (TFA, 0.75 mL) was added to a dichloromethane (1.5 mL) solution of Compound 10. The obtained mixture was stirred at room temperature for 1.5 hours. Thereafter, the solvent was distilled away under reduced pressure to obtain a crude product (red oily substance) containing the title Compound 11. The obtained crude product was used in the subsequent reaction without being subjecting to a further purification operation.

LRMS (ESI): m/z 834 [M+H]$^+$.

2-(2-(2-Azidoethoxy)ethoxy)ethyl(1,33-bis(((2S,3R,4R,5R,6R)-3-acetamide-4,5-dihydroxy-6-(hydroxymethyl)tetrahydro-2H-pyran-2-yl)thio)-17-(16-(((2S,3R,4R,5R,6R)-3-acetamide-4,5-dihydroxy-6-(hydroxymethyl)tetrahydro-2H-pyran-2-yl)thio)-3,14-dioxo-7,10-dioxa-4,13-diazahexadecyl)-3,14,20,31-tetraoxo-7,10,24,27-tetraoxa-4,13,21,30-tetraazatritriacontan-17-yl)carbamate (12)

[Formula 30]

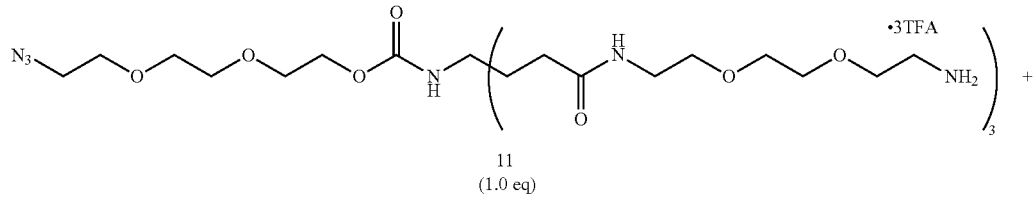

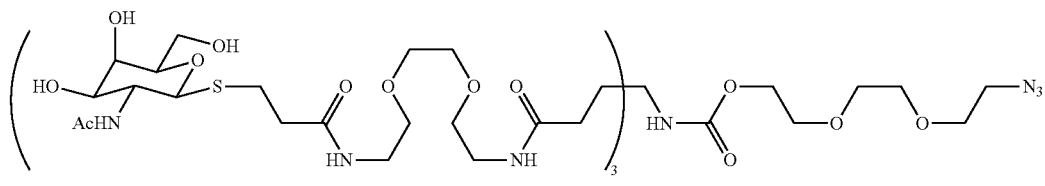

An N,N-dimethylformamide (170 μL) solution of Ammonium Salt 11 (12 mg, 10 μmol) was added to Succinimide 3 (18 mg, 34 μmol) and 1-hydroxybenzotriazole-anhydrous (HOBt anhydrous, 1.1 mg, 8.5 μmol), and thereafter, N,N-diisopropylethylamine (DIPEA, 85 μL) was added thereto. The obtained mixture was stirred at room temperature for 25.5 hours, and the solvent was then distilled away under reduced pressure. After Succinimide 3 had been removed by silica gel chromatography (chloroform/methanol=10:1→8:1), the resultant was eluted with methanol. To the obtained mixture (14.9 mg), sodium methoxide (NaOMe, 2.0 mg, 37 μmol) was added, and the thus obtained mixture was then dissolved in methanol (1.0 mL). The obtained solution was stirred at room temperature for 3 hours, and the solvent was then distilled away under reduced pressure. The obtained crude product was purified by reverse phase silica gel chromatography (water→methanol) to obtain the title Compound 12 (8.0 mg; yield: 46%; a white amorphous substance).

$^1$H NMR (500 MHz, CD$_3$OD) δ: 1.93-1.96 (m, 6H), 1.97 (s, 9H), 2.20-2.23 (m, 6H), 2.56 (dd, 6H, J=7.5, 6.9 Hz), 2.87 (ddd, 3H, J=13.8, 6.9, 6.9 Hz), 3.02 (ddd, 3H, J=13.8, 7.5, 7.5 Hz), 3.36-3.39 (m, 15H), 3.55-3.63 (m, 35H), 3.66 (s, 4H), 3.66-3.73 (m, 6H), 3.81 (dd, 3H, J=11.5, 7.5 Hz), 3.88 (d, 3H, J=2.9 Hz), 4.04 (t, 3H, J=10.3 Hz), 4.12 (brs, 2H), 4.478 (d, 3H, J=10.9 Hz).

(3aS,3a'S,4S,4'S,6aR,6a'R)-4,4'-((((((5-((2-((1-(28-(((2S,3R,4R,5R,6R)-3-Acetamide-4,5-dihydroxy-6-(hydroxymethyl)tetrahydro-2H-pyran-2-yl)thio)-12,12-bis(16-(((2S,3R,4R,5R,6R)-3-acetamide-4,5-dihydroxy-6-(hydroxymethyl)tetrahydro-2H-pyran-2-yl)thio)-3,14-dioxo-7,10-dioxa-4,13-diazahexadecyl)-10,15,26-trioxo-3,6,9,19,22-pentaoxa-11,16,25-triazaoctacosyl)-1H-1,2,3-triazol-4-yl)methoxy)ethyl)carbamoyl)-1,3-phenylene)bis(azanediyl))bis(6-oxohexane-6,1-diyl))bis(azanediyl))bis(5-oxo pentane-5,1-diyl))bis(tetrahydro-1H-thieno[3,4-d]imidazol-2(3H)-iminium)di(2,2,2-trifluoroacetate) (14)

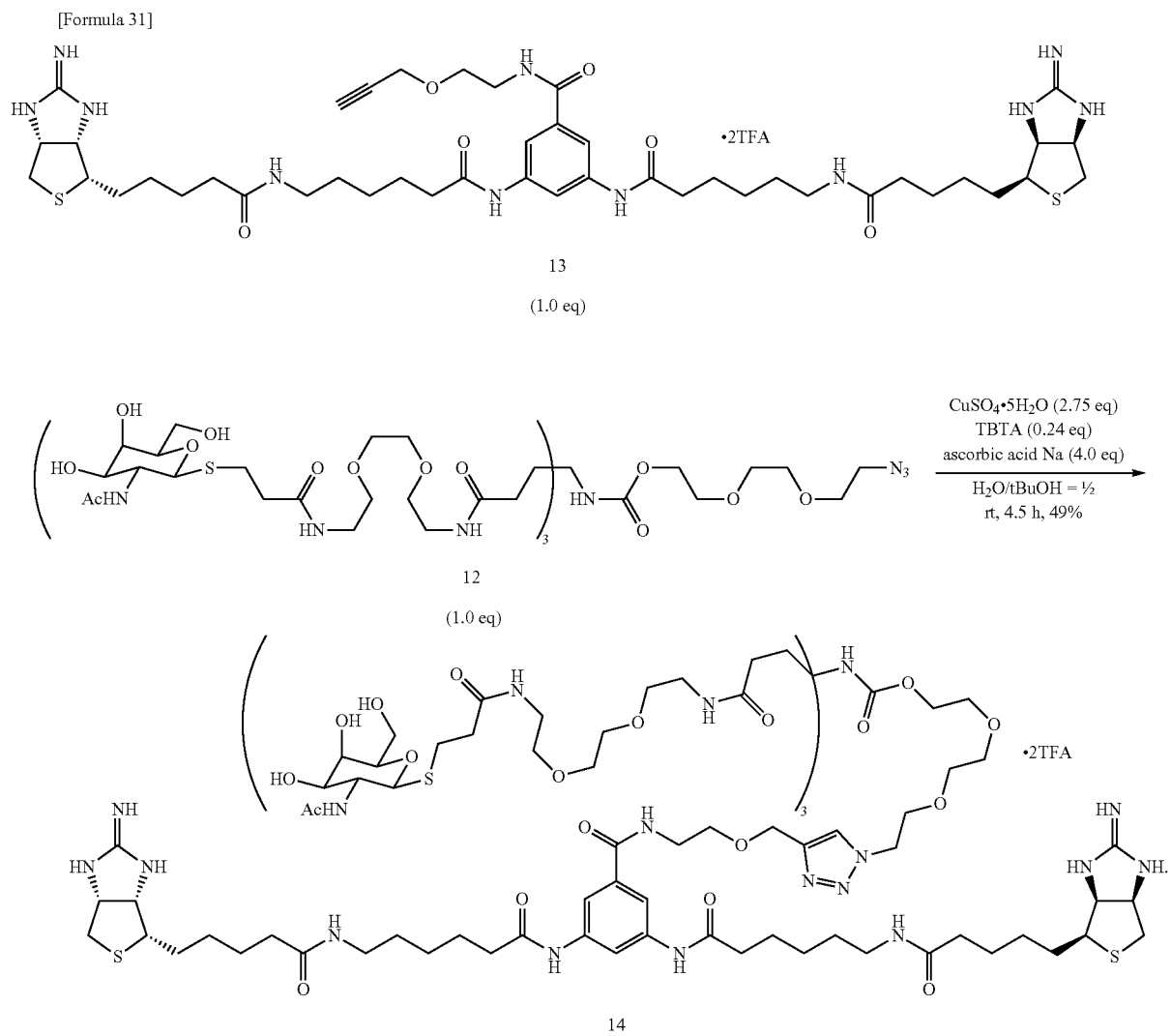

Compound 12 (5.4 mg, 3.2 μmol) was added to Bisiminobiotin 13 (3.6 mg, 3.2 μmol), and thereafter, copper sulfate pentahydrate (CuSO$_4$·5H$_2$O, 2.2 mg, 8.7 μmol), tris[(1-benzyl-1H-1,2,3-triazol-4-yl)methyl]amine (TBTA, 0.4 mg, 7.5 μmol), and sodium ascorbate (ascorbic acid Na, 2.5 mg, 13 μmol) were added thereto. Thereafter, distilled water (100 μL) and tert-butanol (200 μL) were added to the mixture. The obtained mixture was stirred at room temperature for 4 hours, and the solvent was then distilled away under reduced pressure. The obtained crude product was purified by reverse phase HPLC (YMC-Pack YMC-Triart-C18 gradient: 0-20-20.5-60.5-61 min; 0.5-0.5-17.5-57.5-100% CH$_3$CN in 0.1% TFA MQ, ramp time 40 min (17.5-57.5%), $t_R$=35.4 min) to obtain the title Compound 14 (3.9 mg; yield: 49%, a white solid). Compound 14 is also referred to as "Zephyr1."

LRMS (ESI): m/z 875 [M+3H]$^{3+}$.

Dimethyl 6,6'-((5-(3-(2-(2-(2-(pent-4-ynamide)ethoxy)ethyl)ureido)isophthaloyl)bis(azanediyl))(2S,2'S)-bis(2-(5-((3aS,4S,6aR)-2-iminohexahydro-1H-thieno[3,4-d]imidazol-4-yl)pentanamide)hexanoate) di(2,2,2-trifluoroacetate) (23)

[Formula 32]

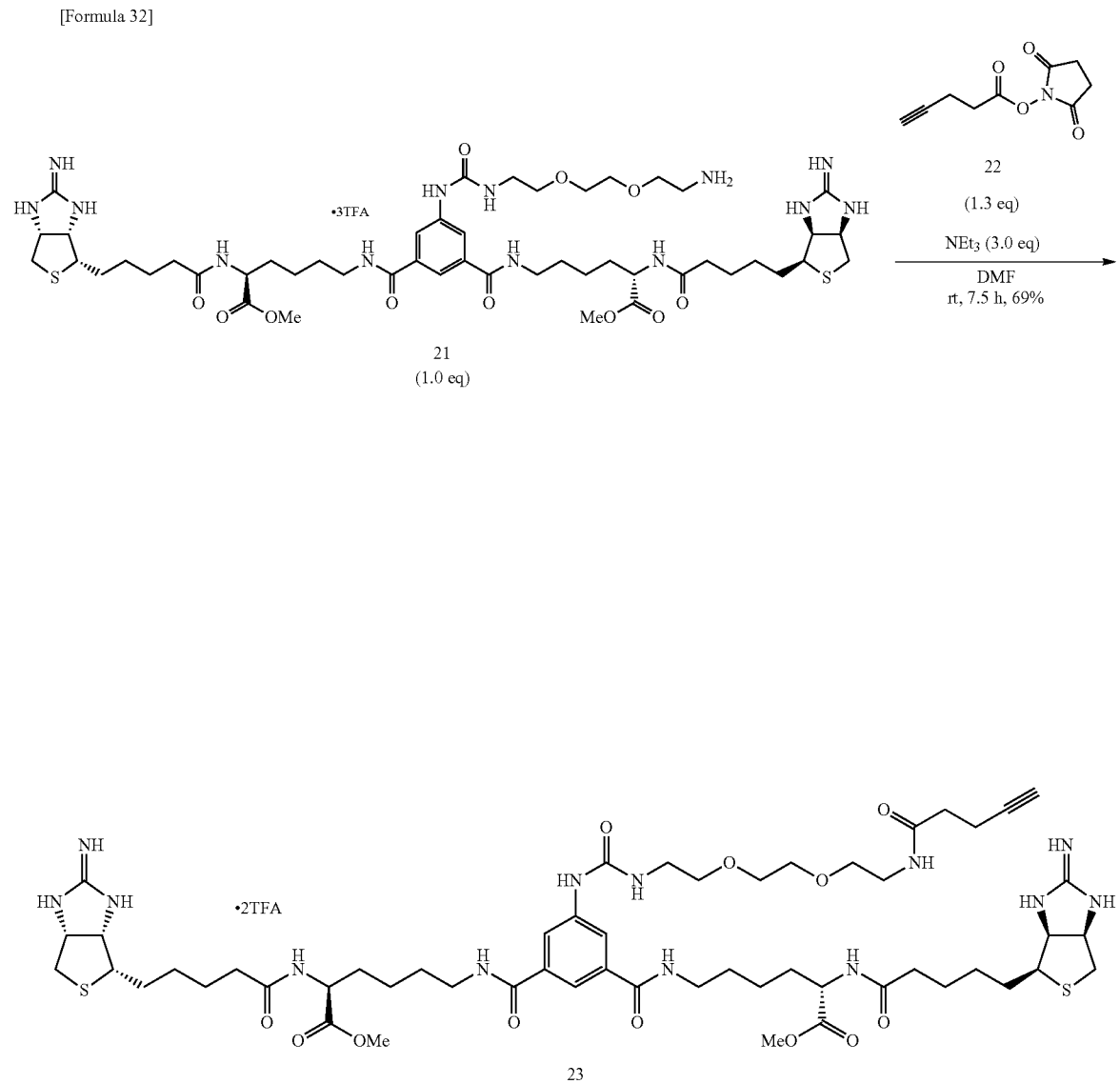

N,N-Dimethylformamide (0.2 mL) and triethylamine (6.4 μL, 0.046 mmol) were added to Bisiminobiotin 21 (21.8 mg, 0.015 mmol) and N-Hydroxy Succinimidyl Ester 22 (3.9 mg, 0.020 mmol). The obtained mixture was stirred at room temperature for 7.5 hours, and the solvent was then distilled away under reduced pressure. The obtained crude product was purified using automated purification equipment (YAMAZEN ODS-SM 50 μm gradient: 0-1-20-25 min; 5-5-80-100% MeOH in 0.1% TFA water), so as to obtain the title Compound 23 (16 mg, 69%, a brown oily substance).

$^1$H NMR (400 MHz, CD$_3$OD) δ: 1.41-1.78 (m, 22H), 1.83-1.92 (m, 2H), 2.24 (d, 1H, J=8.2 Hz), 2.26 (t, 4H, J=2.8 Hz), -(m, 411H), 2.80 (d, 2H, J=10.2 Hz), 2.98 (dd, 2H, J=13.3, 5.0 Hz), 3.23-3.28 (m, 2H), 3.34-3.42 (m, 8H), 3.57 (dt, 4H, J=17.4, 5.5 Hz) 3.64 (s, 4H), 3.70 (s, 6H), 4.40 (dd, 2H, J=9.6, 5.0 Hz), 4.51 (dd, 2H, J=8.2, 4.6 Hz), 4.71 (dd, 2H, J=5.0, 7.8 Hz), 7.81 (s, 1H), 7.95 (d, 2H, J=1.8 Hz)

Dimethyl 6,6'-((5-(3-(2-(2-(2-(3-(1-(28-(((2S,3R,4R, 5R,6R,)-acetamide-4,5-dihydroxy-6-(hydroxymethyl)tetra hydro-2H-pyran-2-yl)thio)-12,12-bis(16-(((2S,3R,4R,5R,6R)-3-acetamide-4,5-dihydroxy-6-(hydroxymethyl)tetrahydro-2H-pyran-2-yl)thio)-3, 14-dioxo-7,10-dioxa-4,13-diazahexadecyl)-10,15,26-trioxo-3,6,9,19,22-pentaoxa-11,16,25-triazaoctacosyl)-1H-1,2,3-triazol-4-yl)propanamide) ethoxy)ethoxy)ureido)isophthaloyl)bis(azanediyl)) (2S,2'S)-bis(2-(5-((3aS,4S,6aR)-2-iminohexahydro-1H-thieno[3,4-d]imidazol-4-yl)pentanamide) hexanoate) di(2,2,2-trifluoroacetate) (25)

[Formula 33]

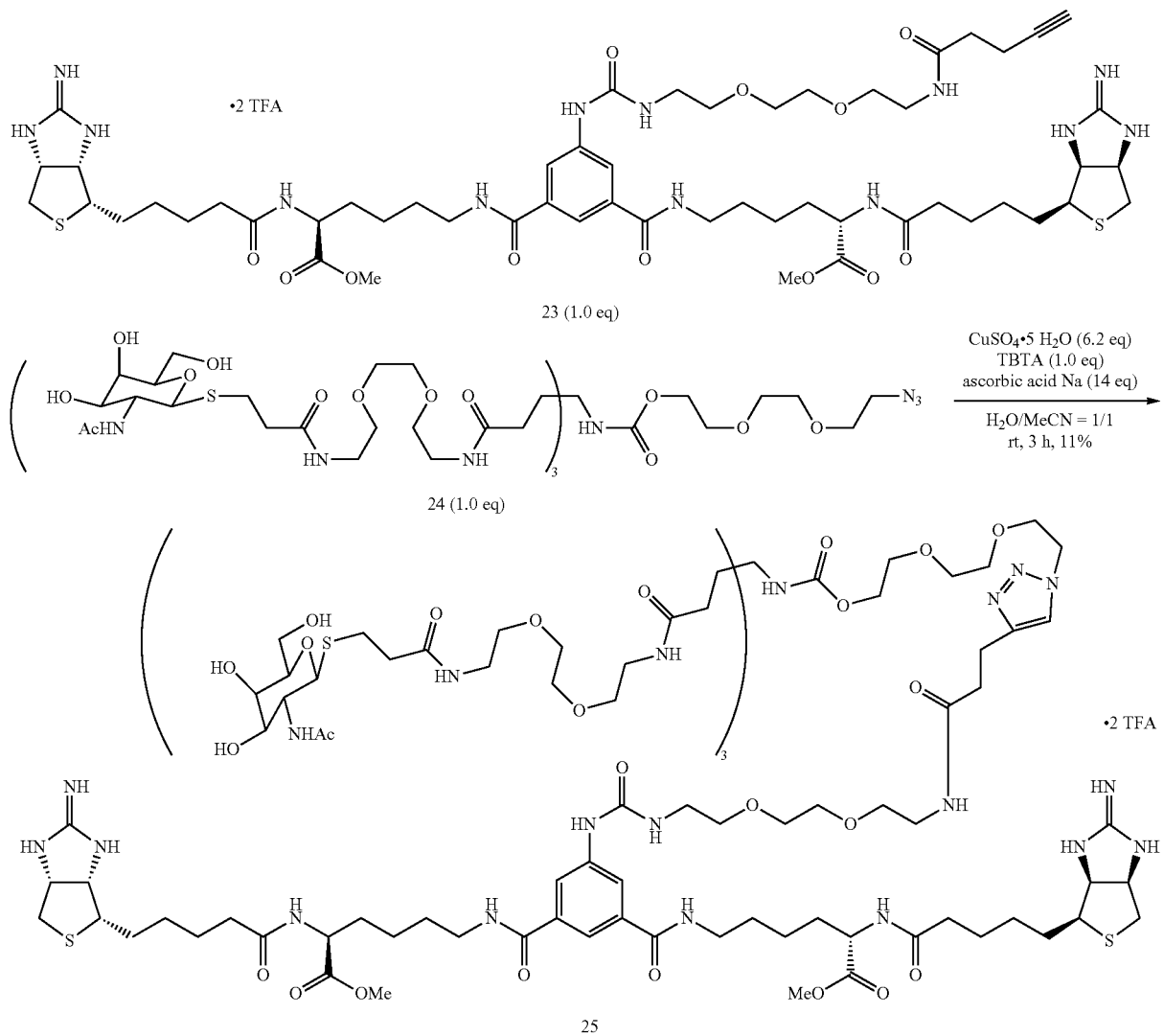

Compound 24 (the same as Compound 12) (2.4 mg, 1.4 μmol) was added to Bisiminobiotin 23 (2 mg, 1.4 μmol), and thereafter, copper sulfate pentahydrate (CuSO$_4$ 5H$_2$O, 2.2 mg, 8.7 μmol), tris[(1-benzyl-1H-1,2,3-triazol-4-yl)methyl] amine (TBTA, 0.8 mg, 1.5 μmol), and sodium ascorbate (ascorbic acid Na, 4.0 mg, 20 μmol) were added thereto. Thereafter, distilled water (100 μL) and acetonitrile (100 μL) were added to the mixture. The obtained mixture was stirred at room temperature for 3 hours, and the solvent was then distilled away under reduced pressure. The obtained crude product was purified by reverse phase HPLC (YMC-Pack YMC-Triart-C18 gradient: 0-20-20.5-60.5-61 min; 5-5-17.5-57.5-100% MeCN in 0.1% TFA MQ, ramp time 40 min (17.5-57.5%), $t_R$=37.2 min), so as to obtain the title Compound 25 (0.5 mg, 11%, a white solid). Compound 25 is also referred to as "Zephyr2."

LRMS (ESI): m/z 721.7 [M+3H]$^{3+}$.

Example 2: Construction of Expression Vector for Anti-CEA-Cupid (ST03-Cupid)

The gene sequence of the scFv-type antibody ST03 that recognizes the N-A1 portion of CEACAM5 was produced based on a publication (U.S. Pat. No. 7,626,011: Antibodies against tumor surface antigens). The gene sequence of ST03-Cupid formed by fusing an ST03 gene with a Cupid gene was produced by artificial gene synthesis (Eurofingenomics) (SEQ ID NO: 1). Cupid is a protein referred to as "V2122," which is described in WO2015/125820 (which is also referred to as "LISA314-V2122") (SEQ ID NO: 4 in WO2015/125820). The amino acid sequence of Cupid is shown as SEQ ID NO: 4 in the sequence listing of the present application.

Next, with reference to a publication (International Publication No. WO 2015125820: Biotin variant, streptavidin mutant, and use thereof), a method comprising allowing the protein skp having chaperone function and the desired protein ST03-Cupid to simultaneously express in *E. coli*, so as to recover the desired protein as a soluble fraction, was carried out. Specifically, the ST03-Cupid gene was incorporated into Multicloning Site 1 (MCS1) of the expression vector pETDuet-1 (Novagen), and the skp gene (SEQ ID NO: 2) was incorporated into Multicloning Site 2 (MCS2) thereof. Incorporation of the ST03-Cupid gene was carried out by treating the vector with the restriction sites NcoI and EcoRI, and then performing ligation and cloning, using the ST03-Cupid gene, which had been amplified using primers (1740_Fw; AGGAGATATACCATGAAATATCTGCTGCCGACCG (SEQ ID NO: 5) and 1741_Rv; CGCCGAGCTCGAATTTTAATGATGGTGATGATGATG (SEQ ID NO: 6)), employing In-Fusion HD Cloning Kit (Clontech). Thereafter, correct incorporation of the ST03-Cupid gene was confirmed by sequencing. Subsequently, the vector, into which the ST03-Cupid gene had been incorporated, was treated with the restriction enzyme NdeI, and then performing ligation and cloning, using the skp gene, which had been amplified using primers (skp Fw; AAGGAGATATACATATGGATAAAATTGCCATTGTTAATAT (SEQ ID NO: 7) and skp_Rv; TTGAGATCTGCCATATGTTATTTCACTTGTTTCAGAACG (SEQ ID NO: 8)), employing In-Fusion HD Cloning Kit (Clontech). Thereafter, correct incorporation of the skp gene was confirmed by sequencing. Thereby, a vector (pETDuet-ST03-Cupid_skp) capable of simultaneously expressing the ST03-Cupid protein and the skp protein was completed.

Example 3: Expression of ST03-Cupid

BL21 (DE3) (Nippon Gene Co., Ltd.) was transformed with the pETDuet-ST03-Cupid_skp vector, and was then pre-cultured in 2×YT medium (BD) at 37° C. overnight. The medium, in which the pre-culture had been performed, was added to a new medium to 100-fold dilution, and the mixture was then cultured at 37° C. until OD (600 nm) became 2.0. Thereafter, IPTG was added to the culture to a final concentration of 0.5 mM, and the obtained mixture was then cultured at 37° C. for 4 hours. Thereafter, the obtained culture was centrifuged, and a culture supernatant was recovered and was then preserved at 4° C.

Example 4: Purification of ST03-Cupid

The ST03-Cupid protein was roughly purified utilizing 6×His-Tag attached to the C-terminus thereof according to a batch method. Specifically, complete His-Tag Purification Resin, which had been equilibrated with buffer A (50 mM Tris-HCl, 0.2 M NaCl, 1 mM EDTA, and 5 mM Imidazole; pH 8.0), was added to the culture supernatant preserved at 4° C., and the obtained mixture was then stirred at 4° C. for 2 hours to overnight, so that a protein-binding treatment was performed on the resin. Subsequently, the resin was recovered in a column, and a 20-column volume washing operation was carried out using buffer A. Thereafter, the resultant was eluted with buffer B (50 mM Tris-HCl, 0.2 M NaCl, 1 mM EDTA, and 400 mM Imidazole; pH 8.0), so that a roughly purified product of ST03-Cupid was recovered.

Subsequently, purification was carried out using a protein L column (Capto L; GE Healthcare). The aforementioned roughly purified product was injected into the column, which had been equilibrated with PBS, and a protein-binding treatment was performed on the resin. Thereafter, the resultant was washed with 20-column volume of PBS, and was then eluted with a 10 mM glycine-HCl buffer (pH 2.1). The eluted protein solution was subjected to a desalination column (PD-10 Column, GE Healthcare) to replace the used solvent with PBS, and was then subjected to an ultrafiltration column (VIVASPIN Turbo 15, Sartorius) for concentration.

Example 5: Production of Iodinated ST03-Cupid

Using N-succinimidyl-3-(4-hydroxy-3-[$^{125}$I]iodophenyl) propionate, Bolton-Hunter Reagent (NEX120, PerkinElmer), the purified ST03-Cupid protein was radio-iodinated. Specifically, Bolton-Hunter Reagent in an amount of 20 times the number of moles of the used protein was taken in an Eppendorf tube, the solvent was then vaporized, and the protein solution was then added thereto. The mixture was reacted on ice for 2 hours. Thereafter, the reaction mixture was subjected to a desalination column (PD MiniTrap G-25, GE Healthcare) to remove unreacted radio-iodination Bolton-Hunter Reagent, and the resultant was then subjected to an ultrafiltration column (VIVASPIN Turbo 4, Sartorius) for concentration. After completion of the concentration, the amount of radioactivity was measured using a dose calibrator (CRC-25w, CAPINTEC), and the quality of the protein was checked by performing CBB staining according to SDS-PAGE.

Example 6: In Vivo Test of Clearing Agent (Compound 14)

In order to examine the efficacy of Compound 14 (Zephyr1), $^{125}$I-labeled ST03-Cupid ([$^{125}$I]ST03-Cupid) was administered to male mice via single intravenous administration, and the blood was then collected over time, so that a change in the blood radioactivity concentration caused by administration of Compound 14 was measured. Specifically, four experimental groups were prepared. In a first group, Compound 14 was administered to the mice via single intravenous administration, 6 hours after administration of [$^{125}$I]ST03-Cupid. A second group was defined as a control group for the first group, and a normal saline was administered to the mice, instead of Compound 14. In a third group, Compound 14 was administered to the mice via single intravenous administration, 24 hours after administration of [$^{125}$I]ST03-Cupid. A fourth group was defined as a control group for the third group, and a normal saline was administered to the mice, instead of Compound 14.

Specifically, with regard to administration of [$^{125}$I]ST03-Cupid to the mice, 100 μL of [$^{125}$I]ST03-Cupid was administered in a concentration of 50 kBq/100 μL to the mice via single intravenous administration (143 μmol/50 kBq/100 μL injection). Thereafter, 6 hours or 24 hours after administration of [$^{125}$I]ST03-Cupid, Compound 14 was administered to the mice in an amount of 2 times the number of moles of the administered ST03-Cupid (286 μmol/100 μL injection), or 100 μL of a normal saline was administered to the mice. It is to be noted that the experiments were carried out using the mice groups (n=4 to 6 in each group).

The blood was collected from the orbital vein of the mice over time. When Compound 14 was administered to the mice 6 hours after administration of [$^{125}$I]ST03-Cupid, blood collection was carried out with the following time intervals: first blood collection—10 minutes after administration of [$^{125}$I]ST03-Cupid, second blood collection—6 hours after administration of [$^{125}$]ST03-Cupid, third blood collection—10 minutes after administration of Saline or Compound 14, fourth blood collection—1 hour after administration of Saline or Compound 14, fifth blood collection—3 hours after administration of Saline or Compound 14, sixth blood collection—18 hours after administration of Saline or Compound 14, and seventh blood collection—24 hours after administration of Saline or Compound 14. Likewise, when Compound 14 was administered to the mice 24 hours after administration of [$^{125}$I]ST03-Cupid, blood collection was carried out with the following time intervals: first blood collection—10 minutes after administration of [$^{125}$]ST03-Cupid, second blood collection—24 hours after administration of [$^{125}$I]ST03-Cupid, third blood collection—10 minutes after administration of Saline or Compound 14, fourth blood collection—1 hour after administration of Saline or Compound 14, fifth blood collection—3 hours after administration of Saline or Compound 14, sixth blood collection—6 hours after administration of Saline or Compound 14, and seventh blood collection—24 hours after administration of Saline or Compound 14. The collected blood (40 to 50 μL) was measured using a gamma counter. The counting rate (dmp) measured with the gamma counter was divided by the amount of blood collected (g) to calculate a counting rate (dpm/g of blood) per unit weight, and the results were shown in a graph. Likewise, the counting rate (dmp) measured with the gamma counter was divided by the counting rate of [$^{125}$I]ST03-Cupid before administration, so as to calculate the remaining percentage (% ID/g of blood) in the dose after the administration. The results were shown in a graph. The measurement results are shown in Tables 1 and 2 and FIGS. 1 and 2. From these results, it was demonstrated that the blood concentration of ST03-Cupid can be efficiently reduced using the clearing agent of the present invention. Thus, the usefulness of the present clearing agent was demonstrated.

TABLE 1

Administration of CA 6 hours after administration of [$^{125}$I] ST03-Cupid

| Time | Radioactivity concentration (dpm/g) | | % Injected Dose/g of blood | |
|---|---|---|---|---|
| (hr) | Control | With CA (6 hr) | Control | With CA (6 hr) |
| 0.17 | 638596 ± 43511 | 599504 ± 68046 | 33.8 ± 2.3 | 31.7 ± 3.6 |
| 5.92 | 318189 ± 20436 | 312854 ± 42382 | 16.8 ± 1.1 | 16.6 ± 2.2 |
| 6.17 | 297804 ± 17523 | 117840 ± 34798 | 15.8 ± 0.9 | 6.2 ± 1.8 |
| 7 | 278874 ± 15873 | 90787 ± 29628 | 14.8 ± 0.8 | 4.8 ± 1.6 |
| 9 | 241122 ± 16672 | 83236 ± 29606 | 12.8 ± 0.9 | 4.4 ± 1.6 |
| 24 | 111541 ± 12650 | 46178 ± 15340 | 5.9 ± 0.7 | 2.4 ± 0.8 |
| 30 | 88840 ± 11653 | 37023 ± 13443 | 4.7 ± 0.6 | 2.0 ± 0.7 |

*Control: Mean and S.D. (n = 6), With CA: Mean and S.D. (n = 5)

TABLE 2

Administration of CA 24 hours after administration of [$^{125}$I] ST03-Cupid

| Time | Radioactivity concentration (dpm/g) | | % Injected Dose/g of blood | |
|---|---|---|---|---|
| (hr) | Control | With CA (24 hr) | Control | With CA (24 hr) |
| 0.17 | 647866 ± 28379 | 638296 ± 48098 | 34.3 ± 1.5 | 33.8 ± 2.5 |
| 23.92 | 126033 ± 4490 | 116201 ± 17325 | 6.7 ± 0.2 | 6.2 ± 0.9 |
| 24.17 | 119257 ± 6013 | 8368 ± 1872 | 6.3 ± 0.3 | 0.4 ± 0.1 |
| 25 | 115219 ± 5696 | 7381 ± 1798 | 6.1 ± 0.3 | 0.4 ± 0.1 |
| 27 | 105880 ± 4911 | 10748 ± 2533 | 5.6 ± 0.3 | 0.6 ± 0.1 |
| 30 | 94261 ± 5448 | 12088 ± 3191 | 5.0 ± 0.3 | 0.6 ± 0.2 |
| 48 | 44105 ± 2161 | 9001 ± 1942 | 2.3 ± 0.1 | 0.5 ± 0.1 |

*Control: Mean and S.D. (n = 4), With CA: Mean and S.D. (n = 4)

Example 7: Measurement of Affinity of Compound 14 (Zhepyr1) and Compound 25 (Zephyr2) to Cupid In order to examine the affinity of Zephyr1 and Zephyr2 to Cupid, kinetics analysis was carried out using SPR (Biacore T200). Specifically, using Amin Coupling Kit (GE Healthcare), CEA-Cupid serving as a ligand was immobilized on Sensor Chip CM5 (GE Healthcare), targeting 5000RU. Thereafter, using 5 two-fold serial dilutions (from 10 nM) of Zephyr1 or Zephyr2 serving as an analyte, kinetics analysis was carried out according to a Single Cycle Kinetics method. Thereafter, using Biacore T200 Evaluation Software, version 2.0 (GE Healthcare), the obtained data were fitted at a Bivalent Analyte mode, and kinetic parameters were calculated. As a result, Zephyr1: $k_a$=3.792E+4, $k_d$=4.42E-6 (FIG. 3A); and Zephyr2: $k_a$=1.578E+7, $k_d$=0.09339 (FIG. 3B). That is to say, Zephyr1: $K_D$=$k_d$/$k_a$=1.167E-10 M; and Zephyr2: $K_D$=$k_d$/$k_a$=5.885E-09 M. From these results, it was confirmed that the affinity of Zephyr2 ($K_D$=5.885E-09 M) to Cupid was reduced by approximately one fiftieth, in comparison to that of Zephyr1 ($K_D$=1.167E-10 M).

Example 8

<Preparation of Psyche-B-DOTA($^{111}$In) as Labeling Substance>

A 100 mM acetate buffer was added to $^{111}$InCl$_3$ solution 37 MBq (approx. 20 μmol) in the same volume as the $^{111}$InCl$_3$ solution, and the pH of the mixed solution was then adjusted to pH 4 to 5. Psyche-B-DOTA was added to the mixed solution at a molar ratio of 1000 times (10 nmol), such that the concentration of DMSO became 0.2% or more. The thus obtained mixture was heated at 80° C. for 15 minutes or more. Thereafter, the reaction mixture was analyzed according to HPLC, and the radiochemical purity was confirmed. The mixture was diluted with a 10 mM acetate buffer to a concentration of 1 nmol/mL, and the obtained solution was used as an administration solution.

<Clearance of Cupid by Zephyr2 In Vivo>

Whether or not Cupid existing in the blood of a living body is cleared by Zephyr2 was examined by performing an experiment using xenograft mouse models. The experiment was carried out using three mice from a Zephyr2 administration group and three mice from a non-administration group (control group). Specifically, 150 μmol CEA-Cupid was administered to the xenograft mouse models, and 20 hours after the administration of CEA-Cupid, 100 μmol Zephyr2 was administered (the control group was untreated). Thereafter, two hours after the administration of Zephyr2, the administration solution Psyche-B-DOTA ($^{111}$In) was administered to the two groups. Subsequently, 4 hours after the administration of the labeling substance, blood was collected, and the amount of radioactivity therein was then measured using a gamma counter. As a result, the amount of radioactivity was found to be 4.51% ID/g in the Zephyr2 administration group, whereas it was found to be 22.09% ID/g in the control group. Thus, the clearance of CEA-Cupid from the blood was confirmed as a result of the administration of Zephyr2 (FIG. 4).

The invention claimed is:

1. A compound of formula (3) or a salt thereof:

[Formula 3]

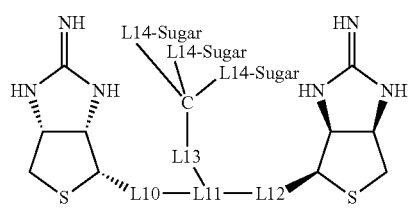

(3)

wherein L10 and L12 each independently represent an alkylene group containing 1 to 10 carbon atoms, —CONH—, —NHCO—, —O—, or a combination thereof; L11 represents a trivalent linking group; L13 represents an alkylene group containing 1 to 10 carbon atoms, —CONH—, —NHCO—, —O—, or a combination thereof, and L13 also comprises a group represented by formula:

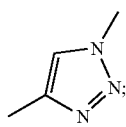

L14 represents an alkylene group containing 1 to 10 carbon atoms, —CONH—, —NHCO—, —O—, or a combination thereof; and Sugar represents a sugar residue.

2. The compound according to claim 1, or a salt thereof, wherein L11 is a group represented by formula:

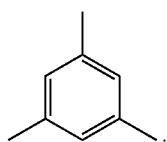

3. A compound selected from the group consisting of:

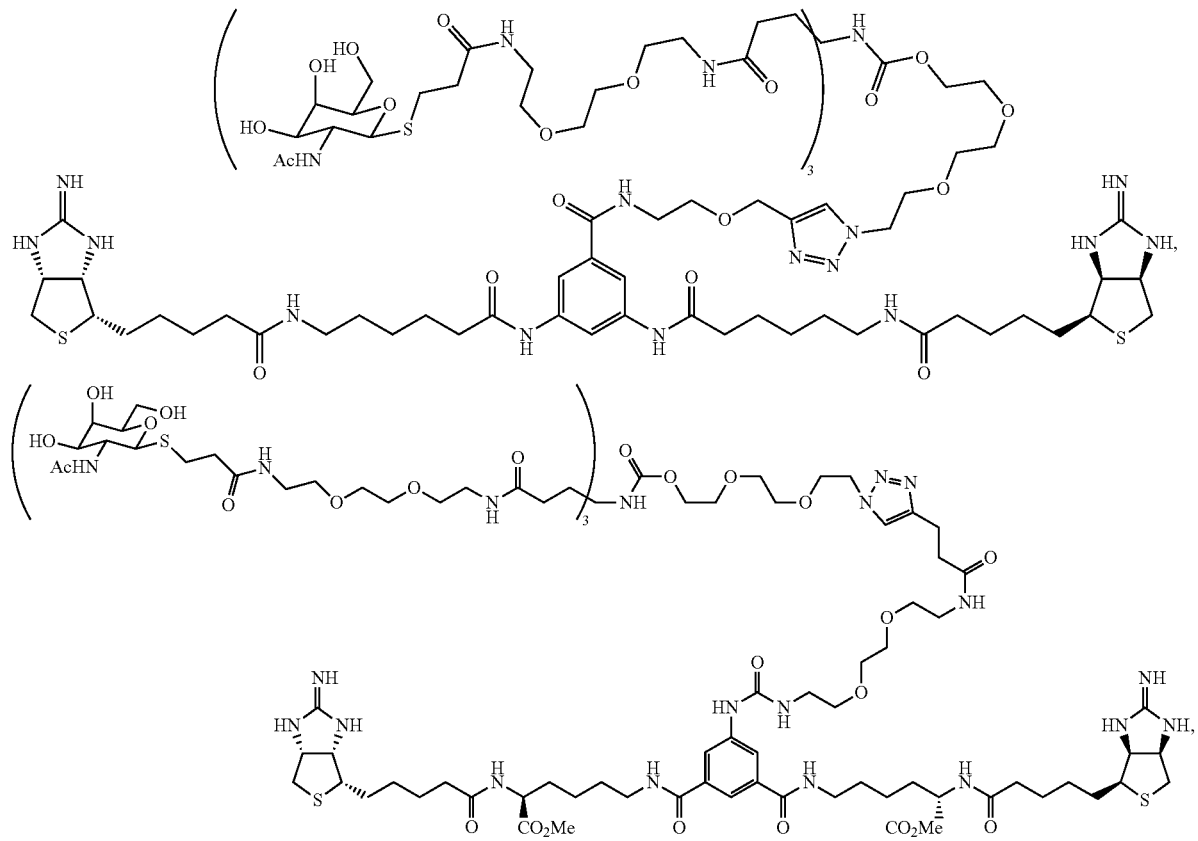

and a salt thereof.

4. A clearing agent for clearing a fusion of a streptavidin mutant and a molecular probe, comprising a compound of formula (3) or a salt thereof:

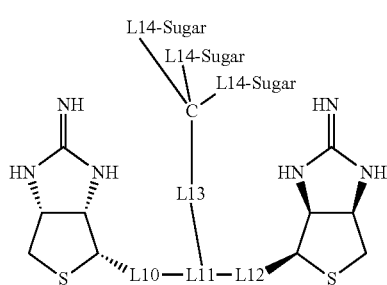

(3)

wherein L10 and L12 each independently represent an alkylene group containing 1 to 10 carbon atoms, —CONH—, —NHCO—, —O—, or a combination thereof; L11 represents a trivalent linking group; L13 represents an alkylene group containing 1 to 10 carbon atoms, —CONH—, —NHCO—, —O—, or a combination thereof, and L13 also comprises a group represented by formula:

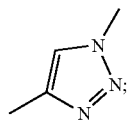

L14 represents an alkylene group containing 1 to 10 carbon atoms, —CONH—, —NHCO—, —O—, or a combination thereof; and Sugar represents a sugar residue.

5. A kit, comprising:
(i) a compound of formula (3) or a salt thereof:

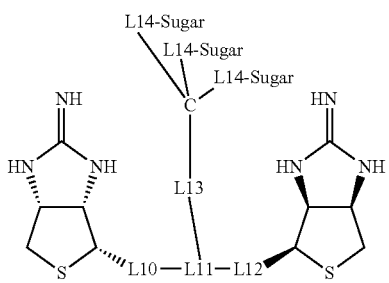

(3)

wherein L10 and L12 each independently represent an alkylene group containing 1 to 10 carbon atoms, —CONH—, —NHCO—, —O—, or a combination thereof; L11 represents a trivalent linking group; L13 represents an alkylene group containing 1 to 10 carbon atoms, —CONH—, —NHCO—, —O—, or a combination thereof, and L13 also comprises a group represented by formula:

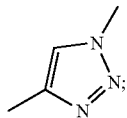

L14 represents an alkylene group containing 1 to 10 carbon atoms, —CONH—, —NHCO—, —O—, or a combination thereof; and Sugar represents a sugar residue, and (ii) a fusion of a streptavidin mutant and a molecular probe,
wherein the streptavidin mutant consists of the amino acid sequence as set forth in SEQ ID NO: 3, in which the amino acid residue at position 37, Asn, is substituted with another amino acid residue, and
wherein the molecular probe is an antibody, peptide, nucleic acid, or aptamer.

6. The kit according to claim 5, further comprising a therapeutic, in vivo diagnostic, or ex vivo diagnostic substance, which is labeled with a compound represented by formula (10):

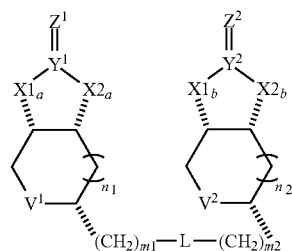

wherein X1a, X1b, X2a and X2b each independently represent O or NH; $Y^1$ and $Y^2$ each independently represent C or S; $Z^1$ and $Z^2$ each independently represent O, S or NH; $V^1$ and $V^2$ each independently represent S or $S^+$—$O^-$; n1 and n2 each independently represent an integer of 0 or 1; m1 and m2 each independently represent an integer from 1 to 10; and L represents a linking group, and wherein the therapeutic, in vivo diagnostic, or ex vivo diagnostic substance is a fluorescent dye, a chemiluminescent agent, a radioisotope, a sensitizer consisting of a metal compound, a neutron capturing agent consisting of a metal compound, a drug, micro- or nano-bubbles, or a protein.

* * * * *

```
SEQUENCE LISTING

<160> NUMBER OF SEQ ID NOS: 8

<210> SEQ ID NO 1
<211> LENGTH: 1230
<212> TYPE: DNA
<213> ORGANISM: Artificial Sequence
<220> FEATURE:
<223> OTHER INFORMATION: Description of Artificial Sequence:
      Artificially Synthetized DNA

<400> SEQUENCE: 1
ccatggatga aatatctgct gccgaccgca gcagcgggtc tgctgctgct ggcagcacag      60
cctgcaatgg cacaggttaa actggaacag agcggtgccg aagttgttaa accgggtgca    120
agcgttaaac tgagctgtaa agcaagcggc tttaacatca aagatagcta tatgcattgg    180
ctgcgtcagg gtccgggtca gcgtctggaa tggattggtt ggattgatcc ggaaaatggt    240
gataccgaat atgcaccgaa atttcagggt aaagcaacct ttaccaccga taccagcgca    300
aataccgcat atctgggtct gagcagcctg cgtccggaag ataccgcagt gtattattgt    360
aatgaaggca ccccgaccgg tccgtattat ttcgattatt ggggtcaggg caccctggtt    420
accgttagca gcggtggtgg tggtagtggt ggcggtggtt caggcggtgg cggtagcgaa    480
aatgttctga cccagagccc gagcagcatg agcgttagcg ttggtgatcg tgttaccatt    540
gcatgtagcg caagcagcag cgttccgtac atgcactggt gcagcagaa accgggtaaa    600 agcccgaaac tgctgattta tctgaccagc aatctggcaa gcggtgttcc gagccgtttt    660
agcggtagcg gtagtggcac cgattatagc ctgaccatta gcagcgtgca gcctgaagat    720
gcagcaacct attattgtca gcagcgtagc agttatccgc tgacctttgg tggtggcacc    780
```

```
aaactggaaa ttaaaggggg tggtggctca ggtggcggag gtgcagaagc aggtattacc    840
ggtacatggt cagatcagct gggtgatacc tttattgtta ccgcaggcgc agatggtgca    900
ctgaccggca cctatgaaaa tgcagttggt ggtgcagaaa gccgttatgt gctgaccggt    960
cgttatgata gcgcaccggc aaccgatggt agcggcaccg cactgggttg gaccgttgca   1020
tggaaaaata acagcaaaaa tgcacatagc gcaaccacct ggtcaggtca gtatgtgggt   1080
ggtgccgatg ccaaaattaa cacccagtgg ctgctgacca gcggtacaac caatgcaaat   1140
gcctggaaaa gtaccctggt tggtcatgat acattccaca agttaaaacc gagcgcagca   1200
agccatcatc atcaccatca ttaagaattc                                    1230
```

<210> SEQ ID NO 2
<211> LENGTH: 420
<212> TYPE: DNA
<213> ORGANISM: Artificial Sequence
<220> FEATURE:
<223> OTHER INFORMATION: Description of Artificial Sequence: skp gene

<400> SEQUENCE: 2

```
gataaaattg ccattgttaa tatgggtagc ctgtttcagc aggttgcaca gaaaaccggt     60
gttagcaata ccctggaaaa tgaatttaaa ggtcgtgcaa gcgaactgca gcgtatggaa    120
accgatctgc aggcaaaaat gaaaaaactg cagagcatga aagcaggtag cgatcgtacc    180
aaactggaaa agatgttat ggcacagcgt cagacctttg cccagaaagc acaggcattt    240
gaacaggatc gtgcacgtcg tagcaatgaa gaacgtggta aactggttac cgtattcag     300 accgcagtta aaagcgttgc aaatagccag gatattgatc tggttgttga tgcaaatgcc    360
gttgcctata tagcagtga tgtgaaagat attaccgcag acgttctgaa acaagtgaaa    420
```

<210> SEQ ID NO 3
<211> LENGTH: 127
<212> TYPE: PRT
<213> ORGANISM: Artificial Sequence
<220> FEATURE:
<223> OTHER INFORMATION: Description of Artificial Sequence: Recombinant
      peptide

<400> SEQUENCE: 3

```
Ala Glu Ala Gly Ile Thr Gly Thr Trp Ser Asp Gln Leu Gly Asp Thr
1               5                   10                  15

Phe Ile Val Thr Ala Gly Ala Asp Gly Ala Leu Thr Gly Thr Tyr Glu
            20                  25                  30

Asn Ala Val Gly Asn Ala Glu Ser Arg Tyr Val Leu Thr Gly Arg Tyr
        35                  40                  45
```

```
Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
 65                  70                  75                  80

Ser Gly Gln Tyr Val Gly Gly Ala Asp Ala Lys Ile Asn Thr Gln Trp
                 85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 4
<211> LENGTH: 127
<212> TYPE: PRT
<213> ORGANISM: Artificial Sequence
<220> FEATURE:
<223> OTHER INFORMATION: Description of Artificial Sequence: Recombinant
      peptide

<400> SEQUENCE: 4

Ala Glu Ala Gly Ile Thr Gly Thr Trp Ser Asp Gln Leu Gly Asp Thr
 1               5                  10                  15

Phe Ile Val Thr Ala Gly Ala Asp Gly Ala Leu Thr Gly Thr Tyr Glu
                 20                  25                  30

Asn Ala Val Gly Gly Ala Glu Ser Arg Tyr Val Leu Thr Gly Arg Tyr
             35                  40                  45

Asp Ser Ala Pro Ala Thr Asp Gly Ser Gly Thr Ala Leu Gly Trp Thr
    50                  55                  60

Val Ala Trp Lys Asn Asn Ser Lys Asn Ala His Ser Ala Thr Thr Trp
 65                  70                  75                  80

Ser Gly Gln Tyr Val Gly Gly Ala Asp Ala Lys Ile Asn Thr Gln Trp
                 85                  90                  95

Leu Leu Thr Ser Gly Thr Thr Asn Ala Asn Ala Trp Lys Ser Thr Leu
            100                 105                 110

Val Gly His Asp Thr Phe Thr Lys Val Lys Pro Ser Ala Ala Ser
        115                 120                 125

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA
```

```
<400> SEQUENCE: 5
aggagatata ccatgaaata tctgctgccg accg                         34

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
cgccgagctc gaattttaat gatggtgatg atgatg                       36

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
aaggagatat acatatggat aaaattgcca ttgttaatat                   40

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
ttgagatctg ccatatgtta tttcacttgt ttcagaacg                    39
```